United States Patent [19]

Seed et al.

[11] Patent Number: 5,955,264
[45] Date of Patent: *Sep. 21, 1999

[54] RAPID MUTATIONAL ANALYSIS METHOD

[75] Inventors: Brian Seed, Boston, Mass.; Andrew Peterson, Durham, N.C.

[73] Assignee: The General Hospital Corporation, Boston, Mass.

[*] Notice: This patent is subject to a terminal disclaimer.

[21] Appl. No.: 08/320,663

[22] Filed: Oct. 11, 1994

Related U.S. Application Data

[60] Division of application No. 07/842,465, Feb. 27, 1992, Pat. No. 5,411,861, which is a continuation-in-part of application No. 07/181,826, Apr. 15, 1988, abandoned.

[51] Int. Cl.$^6$ ...................................................... C12Q 1/68
[52] U.S. Cl. .............................. 435/6; 435/7.1; 435/7.21; 435/7.37; 435/69.1; 435/69.3; 435/91.21; 435/172.1; 435/252.3; 435/270; 435/320.1; 435/325; 436/518; 436/548; 530/388.2
[58] Field of Search ................................ 435/6, 7.1, 69.1, 435/172.3, 91.4, 240.27, 320.1, 7.21, 7.37, 91.21, 172.1, 69.3, 325, 252.3, 270, 849; 530/388.2, 387.2; 436/518, 548, 808; 935/9.1, 16.18, 19, 34; 424/139.1, 141.1

[56] References Cited

U.S. PATENT DOCUMENTS

| | | |
|---|---|---|
| 4,675,285 | 6/1987 | Clark et al. . |
| 4,677,056 | 6/1987 | Dupont et al. . |
| 4,677,061 | 6/1987 | Rose et al. . |
| 5,411,861 | 5/1995 | Seed et al. . |

FOREIGN PATENT DOCUMENTS

| | | |
|---|---|---|
| 0 160 486 | 11/1986 | European Pat. Off. . |
| WO 86/04921 | 8/1986 | WIPO . |

OTHER PUBLICATIONS

Dalgleish et al. (Nov. 7, 1987) "Neutralisation of HIV Isolates by Antiidiotypic Antibodies which Mimic the T4 (CD4) Epitope: a Potential Aids Vaccine", *The Lancet*, pp. 1047–1049.
Williams et al. (1987) "Similarities in Sequences and Cellular Expression between Rat CD2 and CD4 Antigens", *J. Exp. Med.* 165:368–380.
Aruffo et al. (1987) "Molecular Cloning of a CD28 cDNA by a High–Efficiency COS Cell Expression System", *Proc. Natl. Acad. Sci.* 84:8573–8577.
Kemp et al. (1981) "Direct Immunoassay for Detecting *Escherichia coli* Colonies that Contain Polypeptides Encoded by Cloned DNA Segments", *Proc. Natl. Acad. Sci. USA* 78(7):4520–4524.
Rideout et al. (1983) Proceedings of the 5th International Round Table. *Academic Press*, pp. 242–251.
Peterson and Seed (1987) "Monoclonal Antibody and Ligand Binding SItes of the T Cell Erythrocyte Receptor (CD2)", *Nature* 329:842–846.

Bierer et al. (1988) "Expression of the T–cell Surface Molecule CD2 and an Epitope–loss CD2 mutant to Define the Role of Lymphocyte Function–associated Antigen 3 (LFA–3) in T–cell Activation", *Proc. Natl. Acad. Sci. USA* 85:1194–1198.
Paden et al. (1986) "A Flow Cytometric Method for Intracellular Labeling and Purification of Rare Neuronal Populations: Isolation of Fixed Neurophysin Neurons", *Brain Res.* 376:310–319.
Peterson et al. (1988) *Cell* 54:65–72.
Duncan et al. (1982) *J. Bacteriology*:750–755.
Young et al. (1983) *Proc. Natl. Acad. Sci. USA* 80:1194–1198.
Loken et al. (1977) *J. Histochem. Cytochem.* 25:899–907.
Ammerer, G. (1983) "Expression of Genes in Yeast Using the ADCI Promoter", *Meth. Enzymol.* 101:192–201.
Parks et al. (1984) "Flurorescence–Activated Cell Sorting: Theory, Experimental Optimental Optimization and Applications in Lymphoid Cell Biology", *Meth. Enzymol.* 108:197–241.
Botstein et al. (1985) "Strategies and Applications of in Vitro Mutagenesis", *Science* 229:1193–1201.
Kunkel et al. (1985) "Rapid and Efficient Site–specific Mutagenesis without Phenotypic Selection", *Proc. Natl. Acad. Sci. USA* 82:488.
Seed et al. (1983) "Purification of Genomic Sequences from Bacteriophage Libraries by Recombination and Selection in Vitro", *Nuc. Acids Res.* 11:2427–2445.
Levinson et al. (1984) "Minimal Size Plasmids Containing an M13 Origin for Production of Single–Strand Transducing Particles", *J. Mol. and Appl. Genet.* 2:507–517.
Matteucci and Heynecker (1983) "Targeted Random Mutagenesis: the Use of Ambiguously Synthesized Oligonucleotides to Mutagenize Sequences Immediatley 5' of an ATG initiation Codon", *Nucl. Acids Res.* 11:3113–3121.
Deen et al. (1988) "A Soluble Form of CD4 (T4) Protein Inhibits AIDS Virus Infection", *Nature* 331:82–84.
Hunig (1986) "The Ligand of the Erythrocyte Receptor of T Lymphocytes: Expression on White Blood Cells and Possible Involvement in T Cell Activation", *J. Immunol.* 136:2103–2108.
Shaw et al. (1986) "Two Antigen–independent Adhesion Pathways used by Human Cytotoxic T–cell Clones", *Nature* 323:262–264.

(List continued on next page.)

Primary Examiner—Laurie A. Scheiner
Attorney, Agent, or Firm—Greenlee, Winner & Sullivan, P.C.

[57] ABSTRACT

A rapid mutational analysis method for mapping protein epitopes is disclosed. This method has been used to identify the binding sites for 16 anti-CD2 and anti-CD4 monoclonal antibodies. The powerful, rapid, and simple method of the present invention allows isolation of a very large number of mutants, and is applicable to any intracellular or surface protein for which a cDNA and monoclonal antibodies are available. The present method is especially useful in ligand binding site studies for the design of new ligands and drugs.

14 Claims, 12 Drawing Sheets

OTHER PUBLICATIONS

Geysen et al. (1987) "Chemistry of Antibody Binding to a Protein", *Science* 235:1184–1190.

Getzoff et al. (1987) "Mechanisms of Antibody Binding to a Protein", *Science* 235:1191–1196.

Yewdell and Gerhard (1981) "Antigenic Characterization of Viruses by Monoclonal Antibodies", *Ann. Rev. Microbiol.* 35:185–206.

Seed and Aruffo (1987) "Molecular Cloning of the CD2 Antigen, the T–cell Erythrocyte receptor, by a Rapid Immunoselection Procedure", *Proc. Natl. Acad. Sci.* 84:3365–3369.

Meuer et al. (1984) "An Alternative Pathway of T–Cell Activation: A Functional Role for the 50kd T11 Sheep Erythrocyte Receptor Protein", *Cell* 36:897–906.

Chemical Abstract, (1986) vol. 106, p. 360, ref. 3687x.

McDougal et al. (1986) "Biding of the Human Retrovirus HTLV–III/LAV/HIV to the CD4 (T4) Molecule Conformation Dependence, Epitope Mapping, Anitbody Inhibition, and Potential for Idiotypic Minicry", *J. Immunol.* 137(9):2937–2944.

Wysocki et al. (1978) "'Panning' for Lymphocytes: A Method for Cell Selection", *PNAS* 75:2844–2848.

Lasky et al. (1987) "Delineation of a Region of the Human Immunodeficiency Virus Type 1 gp120 Glycoprotein Critical for Interaction with the CD4 Receptor", *Cell* 50:975–985.

Sacerdote et al. (1987) "Vasoactive Intestinal Peptide 1–12: A Ligand for the CD4 (T4)/Human Immunodeficiency Virus Receptor", *J. Neurosci. Res.* 18:102–107.

DiMaio et al. (1982) "Bovine Papillomavirus Vector that Propagates as a Plasmid in both Mouse and Bacterial Cells", *Proc. Natl. Acad. Sci. USA* 79:4030–4034.

Yates et al. (1985) "Stable Replication of Plasmids Derived from Epstein–Barr Virus in Various Mammalian Cells", *Nature* 313:812–815.

U.S.ApplicationNo. 842,865, Feb. 27, 1992, Seed et al.

U.S.application No. 983,647, Dec. 1, 1992, Seed et al.

```
                                                                        60
    KGAVSKEITNALETWGALGQDINLDIPSFQMSDDIDDIKWEKTSDKKKIAQFRKEKETFK
    ┌ 9.6                                           +    0+0+ 00  0
  I │ 7E10                                          +    ++0+ 00  0
    │ MT110                                         0    ++00 =+  +
    └ MT910                                         0    ++00 =+  +

┌ 95-5-49                                       0         00 00
 II │ T11/3PT2H9                                                  =
    └ 35.1                                                      0 =

III │ 9-2                                           +    ++0+ 00  +

120
    EKDTYKLFKNGTLKIKHLKTDDQDIYKVSIYDTKGKNVLEKIFDLKIQERVSKPKISWTC
 II │ T11/3T4-8B5            0    0+0  0  00 0

┌ NU-TER                 +    +0+   +  + 0
    │ CLB-T11/1              0    0+    0  0 0
III │ 39B21                              0  0 00
    │ TS1/8.1.1                     0 0 0 0
    └ F92-3A11                      0 0 0 0

180
    INTTLTCEVMNGTDPELNLYQDGKHLKLSQRVITHKWTTSLSAKFKCTAGNKVSKESSVE
 IV ┌ 9-1                          00
    └ OCH.217                      00

240
    PVSCPEKGLDIYLIIGICGGGSLLMVFVALLVFYITKRKKQRSRRNDEELETRAHRVATE
              ─────────────────────────────────────
                                                                       300
    ERGRKPQQIPASTPQNPATSQHPPPPPGHRSQAPSHRPPPPGHRVQHQPQKRPPAPSGTQ
                      332
    VHQQKGPPLPRPRVQPKPPHGAAENSLSPSSN
```

FIG. 2A

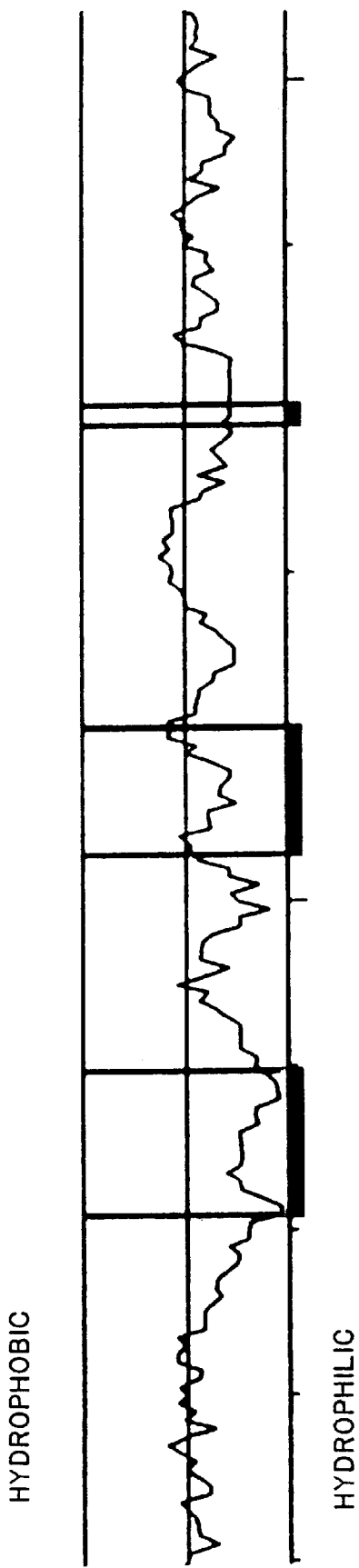

FIG. 3A-1

```
LysThrSerAspLysLysLysIleAlaGlnPheArgLysGluLys          - Mab      + Mab
            Met                                         9.6        35.1
            Asn                                         9.6        35.1
            Glu                                         9.6        35.1
                      Arg                               9.6        35.1
                      Val         Gly                   9.6        35.1

Pro                   35.1       all 16
            Glu                                         MT910      all 16
                                  Pro                   MT910      all 16
                      Asn                               MT110      all 16

Asn                               Thr             95-5-49    all 16
Arg                                                     95-5-49    all 16
                                        Arg             95-5-49    all 16
                            Thr   Pro   Glu             9-2        all 16
                            Asn   Glu                   7E10       all 16
                                        Pro             7E10       all 16
                            Asn         Pro             7E10       all 16
                                        Leu             7E10       all 16
                      Asn                               7E10       all 16
                            Glu         Ile             9.6        35.1
                                                        9.6        35.1
                                                        9.6        35.1
```

(*) indicates position marked above Gln

|  |  |  |  |  |  | 9.6 | 35.1 |
| --- | --- | --- | --- | --- | --- | --- | --- |
| Met | Asn |  | His |  |  | 9.6 | 35.1 |
|  |  |  | ArgSer |  |  | 9.6 | 35.1 |
|  | Met |  | Gln |  |  | 9.6 | 35.1 |
|  | Met |  | Arg |  |  | 9.6 | 35.1 |
| Asn | Asn |  | Leu |  |  | 9.6 | 35.1 |
|  | Pro |  |  |  |  | 9-2 | 35.1 |
|  | Glu |  |  |  |  | 9-2 | 35.1 |
|  |  |  | Leu |  |  | 9-2 | 35.1 |
|  | Gln |  |  |  |  | 9-2 | 35.1 |
|  |  |  | ArgLeu |  |  | 9-2 | 35.1 |
|  | Glu |  | Ile |  |  | 9-2 | 35.1 |
|  | Met |  | Arg |  |  | 9-2 | 35.1 |
|  | Glu |  | Ser |  |  | 9-2 | 35.1 |
|  |  |  | Glu |  |  | 9-2 | 35.1 |
|  | Met |  |  |  |  | 9-2 | 35.1 |
|  | Thr |  | Arg |  |  | 9-2 | 35.1 |
|  | Met |  |  |  |  | 9-2 | 35.1 |
|  | GlnVal |  |  |  |  | 9-2 | 35.1 |
|  | Glu |  | Ile |  |  | 7E10 | 35.1 |
|  |  |  | Leu |  |  | 7E10 | 35.1 |
|  | Glu |  | Ile |  |  | 7E10 | 35.1 |
|  |  |  | Lys |  |  | 7E10 | 35.1 |
| Arg | Glu |  |  |  |  | 7E10 | 35.1 |
|  |  |  | ArgLeu |  |  | 7E10 | 35.1 |
|  |  |  | Arg |  |  | 7E10 | 35.1 |
|  | Gln |  |  |  |  | 35.1 | 7 others |

| Lys | Val | Ser | Ile | Tyr | Asp | Thr | Lys | Gly | Lys | Asn | Val | Leu | Glu | Lys | − Mab | + Mab |
|---|---|---|---|---|---|---|---|---|---|---|---|---|---|---|---|---|
|  |  |  |  | His |  |  |  |  | Glu |  |  | Ile |  | Ser | NU-TER | all 16 |
|  |  |  |  |  |  | Ser |  |  | Val |  |  |  |  |  | T11/3T4-8B5 | all 16 |
|  |  |  | Asp |  |  |  |  |  |  |  |  |  |  |  | CLB-T11/1 | all 16 |
|  |  |  | Asp |  |  |  |  |  |  |  |  |  |  |  | 39B21 | all 16 |
|  |  |  |  |  |  |  |  |  |  |  |  |  |  |  |  |  |
|  | Val |  |  |  |  |  |  |  |  |  |  |  |  |  | NU-TER | all 16 |
|  | Ala |  |  |  |  |  |  |  |  |  |  |  |  |  | NU-TER | all 16 |
|  | Tyr |  |  |  |  |  |  |  |  |  |  |  |  | Phe | NU-TER | all 16 |
|  |  |  |  |  |  |  |  |  |  |  |  |  |  | Ser | NU-TER | all 16 |
| Cys |  |  |  |  |  |  |  |  |  |  |  |  |  |  | T11/3T4-8B5 | all 16 |
|  |  |  |  |  |  |  | Glu |  |  |  |  | Ile | Lys |  | T11/3T4-8B5 | all 16 |
|  |  |  |  |  |  |  |  |  | Lys |  |  |  |  | Lys | T11/3T4-8B5 | all 16 |
| Asp |  |  |  |  |  |  | Ser |  | Val |  |  | Ile |  |  | T11/3T4-8B5 | all 16 |
|  |  |  |  |  |  |  | Glu |  | Lys |  |  |  |  | Lys | T11/3T4-8B5 | all 16 |
|  |  |  |  |  |  |  |  |  |  |  |  |  |  | Ser | CLB-T11/1 | all 16 |
| Cys |  |  |  |  |  |  |  |  |  |  |  |  |  |  | CLB-T11/1 | all 16 |
| Asn |  |  |  |  |  |  |  |  |  |  |  |  |  |  | CLB-T11/1 | all 16 |
|  |  |  |  |  |  |  | Glu |  |  |  |  |  |  |  | CLB-T11/1 | all 16 |
|  |  |  |  |  |  |  | Glu |  |  |  |  |  |  | Ser | CLB-T11/1 | all 16 |
|  |  |  |  |  |  |  |  |  |  |  | Val | Ser |  |  | 39B21 | all 16 |
|  |  |  |  |  |  |  |  |  |  |  |  |  |  | Ser | 39B21 | all 16 |
|  |  |  |  |  |  |  |  |  |  |  |  |  |  | Ser | 39B21 | all 16 |
|  |  |  |  |  |  | Asp |  |  |  |  |  |  |  |  | TS1/8.1.1 | all 16 |
| Cys |  |  |  |  |  |  |  |  | Glu |  |  |  |  |  | TS1/8.1.1 | all 16 |
|  |  |  |  |  |  | Ser |  |  | Val |  |  | Ile |  |  | TS1/8.1.1 | all 16 |

FIG. 4-1

```
                                       *   **    ***            48
                              *        *          *
Leu3a                                 **         *
T4                                     *
94b1
OKT4D
T4/18T3A9                    *
F101-5                  *  **  *
G19-2         KVVLGKKGDTVELTCTASQKKSIQFHWKNWNQIKILG..NQGSFLTKQPS
66.1          TL  E ESA P ES   ITV T FSD R    QHGK  VLIRG  SP

*                 98
                                        *      *
13B.8.2       KLNDRADSRRSLWDQGNFPLLIKNLKIEDSDTYICEVEDQKEEVQLLVFG
VIT4          SQF  F  KKGA EK S    NK  M   Q      L NR    E W  F
OKT4A              *

*                                  147
                             *
BL4/10T4      LTANSDTHLLQGQSLTLTLES.PPGSSPSVQCRSPRGKNIQGGKTLSVSQ
OKT4E         K TFSP T       D NSKV N LTE KHKK  VVS S V  M N
```

FIG. 4-2

```
                     *
OKT4B    LELQDSGTWTCTVLQNQKKVEFKIDIVVLAFQKASSIVYKKEGEQVEFSF  197
         RV   DF N   TLD  NW GMTLS  G STAITA    S    SA

*
NUTH-1   PLAFTVEKLTGSGELWQAERASSSKSWITFDLKNKEVSVKRVTQDPKLQ  247
         N AE ..N W   M K   KD FFQP  S  SI       QKS K L

MGKKLPLHLTLPQALPQYAGSGNLTLALEAKTGKLHQEVNLVVMRATQLQ  297
LKET   T KI  VSL F      T ..DK T       KVA  N
                              *
MT321    KNLTCEVWGPTSPKLMLSLKLENKEAKVSKREKPVWVLNPEAGMWQCLLS  347
         NT    M       MR T Q Q R  EEQ V Q VA   T L

DSGQVLLESNIKVLPTWSTPVQPMALIVLGGVAGLLLFIGLGIFFCVRCR  397
EGDK KMD R Q   SRGVNQTVFL .C      SF F G L C LC

HRRRQAERMSQIKRLLSEKKTCQCPHRFQKTCSPI                442
QQ  A                     PM   SHNL
```

```
   1  GGCGTAATCT GCTGCTTGCA AACAAAAAAA CCACCGCTAC CAGCGGTGGT
  51  TTGTTTGCCG GATCAAGAGC TACCAACTCT TTTTCCGAAG GTAACTGGCT
 101  TCAGCAGAGC GCAGATACCA AATACTGTCC TTCTAGTGTA GCCGTAGTTA
 151  GGCCACCACT TCAAGAACTC TGTAGCACCG CCTACATACC TCGCTCTGCT
 201  AATCCTGTTA CCAGTGGCTG CTGCCAGTGG CGATAAGTCG TGTCTTACCG
 251  GGTTGGACTC AAGACGATAG TTACCGGATA AGGCGCAGCG GTCGGGCTGA
 301  ACGGGGGGTT CGTGCACACA GCCCAGCTTG GAGCGAACGA CCTACACCGA
 351  ACTGAGATAC CTACAGCGTG AGCATTGAGA AAGCGCCACG CTTCCCGAAG
 401  GGAGAAAGGC GGACAGGTAT CCGGTAAGCG GCAGGGTCGG AACAGGAGAG
 451  CGCACGAGGG AGCTTCCAGG GGGAAACGCC TGGTATCTTT ATAGTCCTGT
 501  CGGGTTTCGC CACCTCTGAC TTGAGCGTCG ATTTTTGTGA TGCTCGTCAG
 551  GGGGGCGGAG CCTATGGAAA AACGCCAGCA ACGCAAGCTA GCTTCTAGCT
 601  AGAAATTGTA AACGTTAATA TTTTGTTAAA ATTCGCGTTA AATTTTTGTT
 651  AAATCAGCTC ATTTTTTAAC CAATAGGCCG AAATCGGCAA AATCCCTTAT
 701  AAATCAAAAG AATAGCCCGA GATAGGGTTG AGTGTTGTTC CAGTTTGGAA
 751  CAAGAGTCCA CTATTAAAGA ACGTGGACTC CAACGTCAAA GGGCGAAAAA
 801  CCGTCTATCA GGGCGATGGC CGCCCACTAC GTGAACCATC ACCCAAATCA
 851  AGTTTTTTGG GGTCGAGGTG CCGTAAAGCA CTAAATCGGA ACCCTAAAGG
 901  GAGCCCCCGA TTTAGAGCTT GACGGGGAAA GCCGGCGAAC GTGGCGAGAA
 951  AGGAAGGGAA GAAAGCGAAA GGAGCGGGCG CTAGGGCGCT GGCAAGTGTA
1001  GCGGTCACGC TGCGCGTAAC CACCACACCC GCCGCGCTTA ATGCGCCGCT
1051  ACAGGGCGCG TACTATGGTT GCTTTGACGA GCACGTATAA CGTGCTTTCC
```

FIG. 5-1

```
1101  TCGTTGGAAT CAGAGCGGGA GCTAAACAGG AGGCCGATTA AAGGGATTTT
1151  AGACAGGAAC GGTACGCCAG CTGGATCACC GCGGTCTTTC TCAACGTAAC
1201  ACTTTACAGC GGCGCGTCAT TTGATATGAT GCGCCCCGCT TCCCGATAAG
1251  GGAGCAGGCC AGTAAAAGCA TTACCCGTGG TGGGGTTCCC GAGCGGCCAA
1301  AGGGAGCAGA CTCTAAATCT GCCGTCATCG ACTTCGAAGG TTCGAATCCT
1351  TCCCCCACCA CCATCACTTT CAAAAGTCCG AAAGAATCTG CTCCCTGCTT
1401  GTGTGTTGGA GGTCGCTGAG TAGTGCGCGA GTAAAATTTA AGCTACAACA
1451  AGGCAAGGCT TGACCGACAA TTGCATGAAG AATCTGCTTA GGGTTAGGCG
1501  TTTTGCGCTG CTTCGCGATG TACGGGCCAG ATATACGCGT TGACATTGAT
1551  TATTGACTAG TTATTAATAG TAATCAATTA CGGGGTCATT AGTTCATAGC
1601  CCATATATGG AGTTCCGCGT TACATAACTT ACGGTAAATG GCCCGCCTGG
1651  CTGACCGCCC AACGACCCCC GCCCATTGAC GTCAATAATG ACGTATGTTC
1701  CCATAGTAAC GCCAATAGGG ACTTTCCATT GACGTCAATG GGTGGACTAT
1751  TTACGGTAAA CTGCCCACTT GGCAGTACAT CAAGTGTATC ATATGCCAAG
1801  TACGCCCCCT ATTGACGTCA ATGACGGTAA ATGGCCCGCC TGGCATTATG
1851  CCCAGTACAT GACCTTATGG GACTTTCCTA CTTGGCAGTA CATCTACGTA
1901  TTAGTCATCG CTATTACCAT GGTGATGCGG TTTTGGCAGT ACATCAATGG
1951  GCGTGGATAG CGGTTTGACT CACGGGGATT TCCAAGTCTC CACCCCATTG
2001  ACGTCAATGG GAGTTTGTTT TGGCACCAAA ATCAACGGGA CTTTCCAAAA
2051  TGTCGTAACA ACTCCGCCCC ATTGACGCAA ATGGGCGGAA TTCCTGGGCG
2101  GGACTGGGGA GTGGCGAGCC CTCAGATGCT GCATATAAGC AGCTGCTTTT
2151  TGCCTGTACT GGGTCTCTCT GGTTAGACCA GATCTGAGCC TGGGAGCTCT
2201  CTGGCTAACT AGAGAACCCA CTGCTTAAGC CTCAATAAAG CTTCTAGAGA
2251  TCCCTCGACC TCGAGATCCA TTGTGCTGGC GCGGATTCTT TATCACTGAT
```

FIG. 5-2

2301 AAGTTGGTGG ACATATTATG TTTATCAGTG ATAAAGTGTC AAGCATGACA
2351 AAGTTGCAGC CGAATACAGT GATCCGTGCC GCCCTAGACC TGTTGAACGA
2401 GGTCGGCGTA GACGGTCTGA CGACACGCAA ACTGGCGGAA CGGTTGGGGG
2451 TTCAGCAGCC GGCGCTTTAC TGGCACTTCA GGAACAAGCG GGCGCTGCTC
2501 GACGCACTGG CCGAAGCCAT GCTGGCGGAG AATCATAGCA CTTCGGTGCC
2551 GAGAGCCGAC GACGACTGGC GCTCATTTCT GACTGGGAAT GCCCGCAGCT
2601 TCAGGCAGGC GCTGCTCGCC TACCGCCAGC ACAATGGATC TCGAGGGATC
2651 TTCCATACCT ACCAGTTCTG CGCCTGCAGG TCGCGGCCGC GACTCTAGAG
2701 GATCTTTGTG AAGGAACCTT ACTTCTGTGG TGTGACATAA TTGGACAAAC
2751 TACCTACAGA GATTTAAAGC TCTAAGGTAA ATATAAAATT TTTAAGTGTA
2801 TAATGTGTTA AACTACTGAT TCTAATTGTT TGTGTATTTT AGATTCCAAC
2851 CTATGGAACT GATGAATGGG AGCAGTGGTG GAATGCCTTT AATGAGGAAA
2901 ACCTGTTTTG CTCAGAAGAA ATGCCATCTA GTGATGATGA GGCTACTGCT
2951 GACTCTCAAC ATTCTACTCC TCCAAAAAAG AAGAGAAAGG TAGAAGACCC
3001 CAAGGACTTT CCTTCAGAAT TGCTAAGTTT TTTGAGTCAT GCTGTGTTTA
3051 GTAATAGAAC TCTTGCTTGC TTTGCTATTT ACACCACAAA GGAAAAAGCT
3101 GCACTGCTAT ACAAGAAAAT TATGGAAAAA TATTCTGTAA CCTTTATAAG
3151 TAGGCATAAC AGTTATAATC ATAACATACT GTTTTTTCTT ACTCCACACA
3201 GGCATAGAGT GTCTGCTATT AATAACTATG CTCAAAAATT GTGTACCTTT
3251 AGCTTTTTAA TTTGTAAAGG GGTTAATAAG GAATATTTGA TGTATAGTGC
3301 CTTGACTAGA GATCATAATC AGCCATACCA CATTTGTAGA GGTTTTACTT
3351 GCTTTAAAAA ACCTCCCACA CCTCCCCCTG AACCTGAAAC ATAAAATGAA
3401 TGCAATTGTT GTTGTTAACT TGTTTATTGC AGCTTATAAT GGTTACAAAT
3451 AAAGCAATAG CATCACAAAT TTCACAAATA AAGCATTTTT TTCACTGCAT

FIG. 5-3

```
3501  TCTAGTTGTG GTTTGTCCAA ACTCATCAAT GTATCTTATC ATGTCTGGAT
3551  CCTGTGGAAT GTGTGTCAGT TAGGGTGTGG AAAGTCCCCA GGCTCCCCAG
3601  CAGGCAGAAG TATGCAAAGC ATGCATCTCA ATTAGTCAGC AACCAGGTGT
3651  GGAAAGTCCC CAGGCTCCCC AGCAGGCAGA AGTATGCAAA GCATGCATCT
3701  CAATTAGTCA GCAACCATAG TCCCGCCCCT AACTCCGCCC ATCCCGCCCC
3751  TAACTCCGCC CAGTTCCGCC CATTCTCCGC CCCATGGCTG ACTAATTTTT
3801  TTTATTTATG CAGAGGCCGA GGCCGCCTCG GCCTCTGAGC TATTCCAGAA
3851  GTAGTGAGGA GGCTTTTTTG GAGGCCTAGG CTTTTGCAAA AAGCTAATTC
```

FIG. 5-4

RAPID MUTATIONAL ANALYSIS METHOD

RELATEDNESS OF THE APPLICATION

The subject application is a divisional application of U.S. Ser. No. 07/842,465, filed Feb. 27, 1992, now U.S. Pat. No. 5,411,861, which is a continuation-in-part of U.S. Ser. No. 07/181,826, filed Apr. 15, 1988, now abandoned, which is incorporated herein by reference.

FIELD OF THE INVENTION

This invention is in the field of molecular biology and immunology. It relates to a novel method of selecting for and analyzing mutants. The present invention also relates to the use of this method to identify antigenic domains, epitopes or binding domains of cell surface or intracellular proteins or polypeptides.

BACKGROUND

Resting human T cells bind sheep erythrocytes via a T cell specific 50kD cell surface protein called CD2 (Bach, J. F., et al., Transplantation 8:265–280 (1969); Howard, F. D., et al., J. Immunol. 126:2117–2122 (1981)). This phenomenon has long had practical utility, but, until recently, little known physiological significance. However, parallel studies of the interaction between T cells and sheep erythrocytes (Hunig, T., J. Exp. Med. 162:890–901 (1985); Hunig, T. R., J. Immunol. 136:2103–2108 (1986)), and T cells and their physiological targets (Shaw, S., et al., Nature 323:262–264 (1986)), have led to the identification of a specific molecular ligand for CD2 which is a widely distributed surface protein called, in the human case, LFA-3. CD2/LFA-3 interactions mediate cytolytic target conjugation (Shaw, S., et al., Nature 323:262–264 (1986)), thymocyte-epithelial adhesion (Vollger, et al., (1987)), and the mixed lymphocyte reaction (Martin, P. J., et al., J. Immunol. 131:180–185 (1983)). In addition, a broader role for the CD2 antigen has been suggested by the discovery that certain combinations of anti-CD2-monoclonal antibodies can directly activate mature T cells via an antigen-independent pathway.

An understanding of the molecular interaction between CD2 and LFA-3 or anti-CD2 antibodies would be useful in correlating physiological function with structure. This type of information is useful in designing compounds that can mediate killer T cell or other immune response mechanisms. At present, the most common method for mapping protein epitopes requires the synthesis of an array of short synthetic peptides spanning the protein sequence, and the use of these peptides in multiple binding assays (Geysen, H. M., et al., Science 235:1184–1190 1987)). In order to identify specific residues important for antibody binding, variants of the peptide are synthesized with substitutions at each position. The synthetic peptide strategy has several limitations. If the antibody derives its affinity from interaction with disparate portions of the polypeptide backbone or with a novel conformation of the backbone, the peptide will be unable to mimic the entire protein in binding to the antibody. In order to identify individual residues contacted by the antibody, an extremely large number of peptide variants must be synthesized. The most exhaustive study to date involved the assay of over 1500 individual peptides (Getzoff, E. D., et al., Science 235:1191–1196 (1987)).

Monoclonal antibodies have been used to select against viral envelope determinants (Yewdell, J. W., and Gerhard, W., Ann. Rev. Microbiol. 35:185–206 (1981)). Such selections are both less convenient and less sensitive than desired for the determination of epitope loss mutants because the mutational alterations must be extracted from the viral genome, and mutations leading to viral inviability cannot be detected.

Thus, an efficient method for mapping epitopes or binding domains by identification of epitope or binding domain loss mutants is needed. Such method should utilize an expression host whose viability is not impaired by the introduced mutations. Additionally, the method should permit simple extraction of mutant sequences from the expression host. Further, the method should provide for rapid production, expression and screening of a large number of mutant sequences.

SUMMARY OF THE INVENTION

The present invention relates to a rapid and simple method for mapping protein binding domains including epitopes by identification of substitution mutations that result in the loss of binding capacity. In one embodiment, the rapid mutational analysis technique of the present invention involves the selection of antigen cDNA mutations which lead to a loss of antigen-antibody reactivity. In other embodiments, the rapid mutational analysis technique involves the selection of cDNA encoding protein mutations which lead to a loss of enzyme-substrate or ligand-receptor binding. The method employs cDNA binding domain loss mutants and allows the sampling of a very large number of amino acid substitutions in the native molecule. The mutation frequency is high enough, with the oligonucleotide directed random mutagenesis method used, that rare variants can be efficiently isolated. The technique of the present invention is rapid and simple enough to allow a very large number of mutants to be isolated and can be applied to any surface or intracellular protein for which a cDNA and at least two ligands (e.g., substrates or monoclonal antibodies) are available.

The method of isolating mutant cDNAs encoding protein binding domain loss mutants comprises expressing a vector containing the mutant cDNAs in host cells; exposing the host cell expression products to a negative selection agent (e.g., a first ligand or antibody); discarding those cells containing expression product that binds to the negative selection agent; exposing the host cell expression product to a positive selection agent (e.g., a second ligand or antibody); recovering the host cells whose product binds to the positive selection agent; and recovering vector and cDNA from the recovered host cells. The first ligand or antibody binds to a first binding domain of the native or naturally occurring protein. The second ligand or antibody binds to a second binding domain of the native protein. The selection of host cells which express product that binds only to the positive selection ligand can be accomplished by methods known in the art, e.g., fluorescence activated cell sorting, or by the novel panning method described herein.

The rapid mutation method of the present invention is an oligonucleotide directed random mutagenesis method, in which preselected regions of the cDNA are synthesized with mixtures of wild type and contaminant nucleotide precursors. Preferably, the concentration of said contaminants is selected to produce about one amino acid mutation on average per preselected region and protein. The randomly mutant oligonucleotide is then annealed to a cDNA template, and a duplex cDNA is synthesized. The duplex is amplified under conditions selecting against amplification of the template sequence, and favoring the amplification of the mutant sequence containing the randomly mutant oligonucleotide sequence.

The ability to easily obtain a large number of binding domain loss mutants allows detailed mapping of the accessible surfaces of proteins. The mapping process comprises identifying the nucleotide substitutions by sequencing the cDNAs recovered from host cells expressing product that binds only to the positive selection ligand. The collection of nucleotide substitutions which result in protein binding domain loss for the negative selection ligand define the binding domain for the negative selection ligand.

Using the methods of the present invention, negative selection ligands can be used to identify residues important for ligand or substrate/protein interaction which may occur in pockets inaccessible to antibodies. The identification of ligand binding sites will facilitate structural studies leading to the design of new drugs and ligands that are less antigenic but have greater biological effect.

The method of the present invention has been used to define the regions through which the CD2 antigen binds to anti-CD2 monoclonal antibodies and to define the binding sites on the CD4 antigen for the human immunodeficiency virus (HIV).

CD2 cDNA mutations were selected which lead to loss of CD2-antibody reactivity. The pattern of amino acid substitutions in the mutants defines three distinct regions of the CD2 molecule: one epitopic region recognized by group I and II antibodies; a second epitopic region recognized by group III antibodies; and a third epitopic region recognized by group IV antibodies. Comparison of amino acid residues important for antibody binding and amino acid residues important for LFA-3 binding indicates that group I and II antibodies intersect with one portion of the LFA-3 binding site; that group III antibodies interact with another portion of the LFA-3 binding site; and that group IV antibodies interact with still another portion, which is not involved in LFA-3 binding. In addition, the close correspondence between the effects of individual substitutions on group I antibody and LFA-3 binding suggests that group I antibodies mediate their effect on T cell activation by mimicking the effects of LFA-3 binding.

BRIEF DESCRIPTION OF THE DRAWINGS

FIG. 1A is a representation of the vector piH3MCD2 used for isolation of CD2 mutants.

FIG. 1B is a schematic representation of the strategy for isolation of mutants. In step (i) host cells expressing mutant and wild-type proteins/peptides are treated with a ligand recognizing the binding domain whose loss is desired. Those cells which still express the binding domain bind the ligand, which leads to subsequent complement fixation (step ii) and cell lysis. In step (iii) the remaining cells are treated with a second ligand recognizing a second binding domain of the protein and allowed to adhere to dishes coated with antibody recognizing the second ligand. Only those cells which express the second binding domain bind to the dishes (iv). Plasmid DNA is recovered from the adherent cells. The first step removes those proteins/peptides which still express the binding domain whose loss is desired; the second step increases the efficiency of the procedure and ensures that nontransformants or nontransfectants are not obtained.

FIGS. 2A–2B indicate the location of epitopes on the primary CD2 sequence.

FIG. 2A presents the predicted sequence of the mature CD2 protein. The transmembrane region is underlined with a dark bar. The antibodies used are shown along the left margin. The symbols under the primary sequence indicate the sensitivity of each antibody to changes at that position. A "O" indicates that a mutant was obtained with a substitution at that position or that indirect immunofluorescence of mutants obtained with another antibody showed a sensitivity to substitution at that position. A "+" indicates that a substitution at that position was tested and was not found to affect antibody reactivity. The "=" symbol means that only proline at that position affected reactivity.

FIG. 2B is a hydrophobicity plot for the CD2 protein. Above the central horizontal line are hydrophobic regions; below are hydrophilic regions. The three epitopic regions identified in the mutagenesis experiments are indicated by the heavy bars below the plot.

FIGS. 3A–3B present the mutant collection defining epitope regions of CD2. The sequence of short stretches of the CD2 polypeptide which include each of the two major epitopic regions are shown. The amino acid substitution variants acquired by mutant selection are shown underneath each wild-type sequence. FIG. 3A presents the sequence of epitope region 1 of the CD2 polypeptide. FIG. 3B presents the sequence of epitope region 2 of the CD2 polypeptide. The columns on the right indicate (from left to right) the antibody used for negative selection and the antibody(ies) used for positive selection. "All 16" means that all 16 of the monoclonals in FIG. 2A were combined for the positive selection step. "7 others" means that seven antibodies other than 35.1 recognizing the first epitopic region were combined for the positive selection step. The variants directly under the CD2 sequence were obtained by selecting mutants from a pool of plasmids mutagenized throughout the portion of the cDNA encoding the extracellular domain of the protein. The variants under the bars indicate mutants acquired by selection using plasmid mutagenized only by oligonucleotides covering the span of bars.

FIGS. 4-1 and 4-2 present the location of epitopes on the primary CD4 sequence. The predicted sequence of the CD4 protein is shown, along with the proposed HIV binding site, also termed the Leu3a epitope (overlined), the transmembrane region (underlined) and the amino acid positions where mutant substitution occurs(*).

FIGS. 5-1 and 5-4 present the nucleotide sequence of the piH3M vector. There are 7 segments. Residues 1–587 are from the pBR322 origin of replication, 588–1182 from the M13 origin, 1183–1384 from the supF gene, 1385–2238 from the chimeric cytomegalovirus/human immunodeficiency virus promoter, 2239–2647 from the replaceable fragment or stuffer, 2648–3547 from plasmid pSV2 (splice and polyadenylation signals), and 3548–3900 from the SV40 virus origin.

DETAILED DESCRIPTION

Figure 1A:
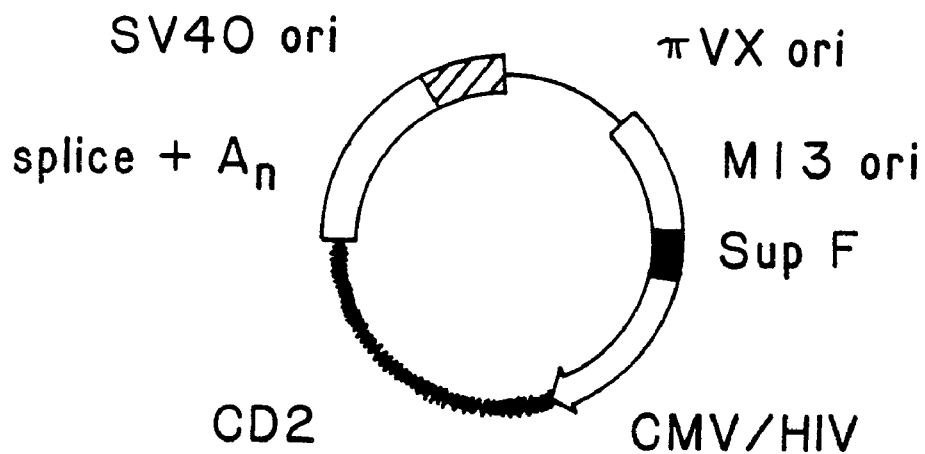
FIGS. 1A–1B are schematic representations of the mutant isolation vector and the procedure for mutant isolation.

The present invention comprises a method for isolation of cDNA encoding binding domain loss mutants useful in binding domain mapping, and an oligonucleotide directed random mutagenesis method that finds application in the subject binding domain mapping method. The subject method makes it possible to map binding domains of any cell surface or intracellular protein for which a cDNA and at least two ligands are known. The subject method allows for the rapid production and screening of a large number of proteins or peptides having amino acid substitutions in the native (naturally occurring) molecule, and thus makes it possible to map the accessible surfaces of proteins, identify ligand binding sites and design proteins which are less antigenic than their natural counterparts, but have greater biological activity.

The essential steps of the present invention for isolation of cDNA encoding binding domain loss mutants comprise: expressing mutant cDNA containing vectors in transformed host cells, treating host cell expression product with a negative selection agent comprising a ligand directed to a first binding domain whose loss is desired, treating host cell expression product with a positive selection agent comprising a ligand directed to a second binding domain, and recovering cells expressing mutant proteins which do not bind to the negative selection ligand, but do bind to the positive selection ligand.

Once the cells expressing vector/cDNA constructs encoding the desired binding domain loss mutants are recovered, vectors are recovered from the cells and the mutant vector/cDNA constructs can be transformed into prokaryotic hosts for amplification prior to sequencing. If a higher yield of mutants is desired, the amplified vectors can then be transfected back into the expression hosts for additional rounds of positive and negative selection prior to cDNA sequencing. Also prior to sequencing of selected vector cDNA, mutant protein expressed in host cells can be scored for substrate or antibody binding. Sequencing of a number of binding domain loss mutant cDNAs allows identification of those nucleotide mutations resulting in loss of ligand binding, and in so doing, defines or maps the binding domain.

A "binding domain loss mutant" is a protein that through mutation in a binding domain has lost the capacity to bind to an antibody, a substrate or other ligand. "Ligand" as used herein refers to an antibody, substrate or any protein or glycoprotein that binds to the target protein at a binding domain. A "binding domain" of a target protein refers to the one or more amino acids directly involved in binding of the target protein to a ligand. The cDNA sequence encoding the protein of interest can be of eukaryotic or prokaryotic origin. The cDNA is a nucleotide sequence encoding a protein or polypeptide, and which typically does not contain intron or promoter sequences.

By "cell surface antigen" or "cell surface protein" is meant a protein that is present on the cell surface; in general, a cell surface antigen is transported through the intracellular membrane system to the cell surface. Such proteins are usually anchored to the cell surface membrane through a hydrophobic domain that lies in the lipid bilayer of the cell. As described herein, the method of the present invention has been used to identify the ligand binding sites of such cell surface proteins as CD2 and CD4 proteins.

By "intracellular protein" is meant a protein that resides within the cell interior. An intracellular protein may be soluble in the cytoplasm and/or anchored to intracellular membrane systems or to the inner leaflet of the plasma membrane.

The negative and positive selection steps can be carried out by, e.g., fluorescence activated cell sorting (FACS) or by the novel panning method depicted in FIG. 1 and described herein.

As is known in the art, FACS can be used to sort cells by fluorescence labeling of cell surface or intracellular proteins. For sorting of cells according to intracellular proteins, the cells must first be made porous prior to treatment with negative and positive selection ligands. See, e.g., Paden, C. M et al. (1986) Brain Res. 376:310–319, incorporated herein by reference. FACS can also sort cells on the basis of two different fluorescence labels directed to intracellular or cell surface proteins. See, e.g., Loken, M. R. et al. (1977) J. Histochem. & Cytochem. 25:899–907. For a discussion of FACS principles and techniques, see Parks, D. R. & Herzenberg, L. A. (1984) Meth. Enzymol. 108:197–241, incorporated herein by reference.

The recovery of host cells expressing cell surface protein binding domain mutants can also be accomplished by the novel panning method illustrated in FIG. 1B. The host cells expressing mutant cell surface proteins are exposed to a negative selection agent, e.g., a first monoclonal antibody directed to a first epitope. The first antibody-complexed cells are then treated with complement under conditions that cause cell lysis. Next, the remaining unlysed cells are exposed to a positive selection agent, e.g., a second monoclonal antibody directed to said second binding domain. Then the second antibody-complexed host cells are recovered by panning with a support coated with a third antibody directed to the second antibody. Vector/cDNA constructs are recovered from the panned host cells. The vector/cDNA constructs are amplified, typically in a prokaryotic host. It is preferred that the vector/cDNA contain a marker suitable for selection of transformed amplification hosts.

The steps of the present invention can be carried out using any suitable eukaryotic or prokaryotic vector-host system. As exemplified herein, the piH3M vector and COS cells comprise a suitable and preferred vector-host system. A suitable vector is one which is capable of amplifying and expressing the mutant cDNA in the eukaryotic and/or prokaryotic host cells. Thus, the vector must contain an expression host compatible promoter and translation terminator (e.g., polyA and splicing domain located 3' to the inserted cDNA), and an amplification host origin of replication. For ease of isolation of transformed amplification host cells, it is preferred that the vector contain a marker gene. For ease of isolation of the mutant cDNA of interest, it is preferred that the vector be stably maintained extrachromosomally. It is also preferred that the vector contain appropriate restriction sites for insertion of the mutant cDNA between the expression host compatible promoter and the translation terminator. Additional preferred, but optional, features of the vector include an M13 bacteriophage origin which allows production of single-stranded template plasmid DNA useful in oligonucleotide directed mutagenesis and in sequencing.

The exemplified piH3M vector contains all of the essential and preferred features. The sequence of PiH3M is presented in FIG. 5, and piH3M is described in Applicants' U.S. Pat. No. 5,506,126 incorporated herein by reference. Its SV40 origin permits replication, and its cytomegalovirus enhancer, HIV promoter sequences, and SV40 splice and polyA signals permit expression of mutant cDNA in COS cells. Its polylinker provides restriction sites for the insertion of cDNA of interest. Its piVX origin allows replication in *E. coli*, while its supF permits selection of transformed *E. coli* by suppression of amber mutations. Finally, its M13 origin permits production of single-stranded template in M13 infected *E. coli.*

However, other known prokaryotic and eukaryotic expression and amplification vector-host systems are available for the practice of the subject method. For example, the Epstein Barr Virus (EBV) derivative plasmids, such as pHEBo2 derivatives, are capable of replication and expression in several human, monkey and dog cell lines and of amplification in *E. coli* (Yates, J. L. et al. (1985) Nature 313:812, incorporated herein by reference). EBV derivative plasmids containing the oriP and EBNA-1 genes are capable of replication in several mammalian host cells. The ampicillin resistance gene is available for selection of transformed *E. coli.* pHEBo2/EBNA-1 derivatives can be stably maintained in various mammalian cell lines (see Table 2 of Yates et al., supra). As exemplified herein, to avoid expression of fusion proteins, a linearized piH3M/cDNA can be used as an expression cassette by insertion of the linearized piH3M/cDNA into a pHEBo2/EBNA-1 derivative such as p205 at its pBR322-derived EcoRI restriction site.

Additionally, as exemplified herein, the subject method can be carried out using bovine papilloma virus (BPV) derivative plasmids expressed in murine C127 cells (DiMaio et al. (1982) PNAS 79:4030–4034, incorporated herein by reference).

The subject method can also be carried out in non-mammalian eukaryotic vector-host systems. As exemplified herein, 2 $\mu$ derivative vectors can be used to express mutant cDNAs of interest in yeast. Specifically, binding domain loss mutants can be isolated by practicing the subject method with pAAH5/cDNA constructs expressed in S. cerevisiae. See Ammerer, G. (1983) Meth. Enzymol. 101:192, incorporated herein by reference.

Further, the subject method can be carried out by expressing the mutant cDNA of interest in prokaryotic hosts. See, e.g., Williams, D. M. et al. (1981), supra, incorporated herein by reference. As exemplified herein, prokaryotic expression hosts can be used where the cDNA of interest encodes a protein that does not require glycosylation for binding function.

The cDNA of interest is randomly mutated by methods known in the art such as by treatment with chemical mutagen, irradiation during replication, or passage through error-inducing (mutator) cell lines. For a review of mutagenesis procedures, see Botstein, D. and Shortle, D. (1985) Science 229:1193–1201, incorporated herein by reference. However, the preferred mutation method is the oligonucleotide directed random mutagenesis method of the subject invention.

The oligonucleotide directed random mutagenesis method of the subject invention provides for rapid generation of a large number of mutant cDNAs encoding proteins which contain preselected domains with only one or a few amino acid mutations. The production of a large number of mutant proteins each having one or a few random mutations in preselected regions is particularly useful in mapping binding domains because single amino acid mutations can be correlated to loss of binding function, allowing for precision mapping of binding domains. The preselected region for random mutagenesis is one which is believed to contain a binding site or epitope. A preliminary assessment of a preselected region can be accomplished by any methods known in the art including hydropathicity analysis of the protein sequence. As exemplified herein, the preselected region of a cell surface protein such as CD2 can comprise the entire extracellular domain. Where a sequence encoding the extracellular domain exceeds 80 nucleotides, the limitations of DNA synthesis technology may require the synthesis of a number of shorter overlapping oligonucleotides of, e.g., 33 nucleotides each, which span the preselected region. In the method exemplified herein, 20 overlapping 33mers which spanned the entire extracellular domain of CD2 were synthesized; each oligonucleotide overlapped its neighbor by 3 nucleotides. When the oligonucleotides are synthesized on a DNA synthesizer as exemplified herein, overlapping of at least one nucleotide at each end of the oligonucleotides is necessitated by the difficulty of adulterating the 3' nucleoside fixed to the column, and the apparently low frequency of mutation at the 5' end.

The random mutagenesis of the oligonucleotide is accomplished by providing mixtures of wild-type and "contaminant" phosphoramidites in reservoirs of the DNA synthesizer. The contaminant phosphoramidites are selected from the three phosphoramidites other than the wild-type phosphoramidite. The four phosphoramidites contain adenosine, thymidine, cytosine and guanosine. Any combination of contaminant phosphoramidites may be used to contaminate one or more reservoirs. The concentration of contaminant phosphoramidites is selected so as to provide a theoretical low number of amino acid mutations in the resulting protein. As exemplified herein, a 5% total contaminant concentration (about 1.7% of each contaminant phosphoramidite) in each reservoir was used to generate 33mer oligonucleotides. The 5% total contaminant concentration resulted in 33mers encoding 1 amino acid mutation on average. A 5% (rather than a 3%) contaminant concentration results in about 1 amino acid substitution per 33 mer oligonucleotide because of the degeneracy of the genetic code. In general, it is preferred that the contaminant concentration and the length of the oligonucleotide be selected so as to maintain the theoretical amino acid mutation frequency at about 1 per oligonucleotide and protein on average. Thus, if overlapping 60mer oligonucleotides spanning the preselected region are synthesized, the reservoir contaminant concentration should be about 2.5%, resulting in a theoretical mutation frequency of 2.5% for each nucleotide in the 60mer, a theoretical 1.5 nucleotide substitution per 60mer, and a theoretical mutation frequency for each 60mer expression product and protein of about 1.

If more than one amino acid substitution on average per protein is desired, the total contaminant oligonucleotide concentration can be increased up to 20%. Since large numbers of mutant proteins can be produced by the subject method, it is preferred for purposes of precision mapping of binding sites, that the mutagenesis method be adapted to produce only one amino acid substitution on average per oligonucleotide and protein. However, rapid generation of proteins each having more than one amino acid substitution in a preselected region are useful in making preliminary assessments of regions likely to contain an epitope or binding domain.

Following synthesis, the randomly mutated oligonucleotide is annealed to a wild type template of the cDNA under relaxed stringency using methods known in the art (see, e.g., Example 1). For ease of synthesis of the duplex cDNA, the template is located within a covalently closed single-stranded circular DNA or plasmid molecule. A double-stranded closed plasmid is then synthesized from the oligonucleotide hybrid using DNA polymerase or reverse transcriptase and ligase. The duplex plasmid contains a heteroduplex cDNA with a wild type template strand and a mutant strand. See Botstein, D. & Shortle, D. (1985), supra.

The single-stranded plasmid containing the cDNA template can be synthesized by methods known in the art. However, to improve efficiency, it is preferred that the template-containing plasmid contain an M13 origin of replication and be synthesized in a host cell infected with M13. When synthesized in this manner, the resulting single-stranded template is relatively free of complementary sequences. Further, in order to provide a means for selection of mutant strand duplexes from wild-type template strand duplexes during subsequent amplification of the heteroduplex cDNA, it is preferred that the template-containing strand contain uracil substitutions. See Kunkel et al. (1985) PNAS 82:488, incorporated herein by reference. Preferably, the percentage of uracil substitutions for thymine in the single-stranded M13 derivative plasmid should be at least about 1%. Uracil-containing templates are produced in E.

coli carrying the Dut– and Una– mutations. The Dut– mutation leads to a deficiency in dUTPase, resulting in a greatly increased pool of dUTP. Some of the dUTP is incorporated into DNA in place of dTTP. The Ung– mutation results in defective or deficient uracil-N-glycosylase, which removes uracil residues that have been incorporated into DNA. Therefore, in Dut–Ung– strains infected with M13, the amplified template contains a small fraction of uracil substitutions for thymine.

The heteroduplex cDNA-containing plasmid is then amplified under conditions that select against the uracil containing template. For example, the heteroduplex can be amplified in vitro after treatment with uracil-N-glycosylase, which removes the uracil, generating sites that block DNA synthesis and which are susceptible to cleavage by nucleases. Additionally, the heteroduplex can be amplified in vivo by transformation into an Ung+ strain. In either case, the template strand is destroyed and production of wild-type sequences is suppressed.

As exemplified herein, where the amplification of the heteroduplex plasmid is carried out in Ung+ E. coli, the plasmid should contain a selection marker gene. In the exemplified piH3M plasmid, the supF gene permits growth of transformed E. coli 1061/p3 in ampicillin and tetracycline. The p3 plasmid contains amber mutated ampicillin and tetracycline resistance genes. Seed, B. (1983) Nucl. Acids Res. 11:2427–2445; Levinson, A. et al. (1984) J. Molec. & Appl. Genet. 2:507–517, both of which are incorporated herein by reference. E. coli 1061 is a non-suppressing strain. Thus transformation of E. coli 1061/p3 with piH3M/cDNA results in expression of both ampicillin and tetracycline resistance.

The oligonucleotide directed random mutagenesis method described hereinabove has the advantage of rapidly producing numerous cDNAs having randomly mutagenized preselected regions. The advantages of this method are believed to flow from the combination of uracil-containing templates and targeted random oligonucleotide mutagenesis. Further, when the vector is constructed to have restriction sites flanking the inserted cDNA, the subject mutagenesis method has the advantage of producing a transferable duplex mutant cDNA, i.e., an entire mutant coding sequence cassette that can be transferred to other vectors. Methods such as those described in Matteucci, & Heynecker, (1983) Nucl. Acids Res. 11:3113–3121, do not provide this advantage.

In the following detailed description, reference will be made to various methodologies known to those of skill in the art of recombinant genetics. Publications and other materials setting forth such known methodologies to which reference is made are incorporated herein by reference.

Standard reference works setting forth the general principles of recombinant DNA technology include Darnell, J. E., et al., Molecular Cell Biology, Scientific American Books, Inc., publisher, New York, N.Y. (1986); Lewin, B. M., Genes III, John Wiley & Sons, New York (1987); Old, R. W., et al., Principles of Gene Manipulation: An Introduction to Genetic Engineering, Second Edition, University of California Press, Berkeley, Calif. (1981); and Maniatis, T., et al., Molecular Cloning: A Laboratory Manual, Cold Spring Harbor Laboratory, Cold Spring Harbor, N.Y. (1982).

Determination of CD2 LFA-3 and Antibody Binding Domains

Figure 1B:
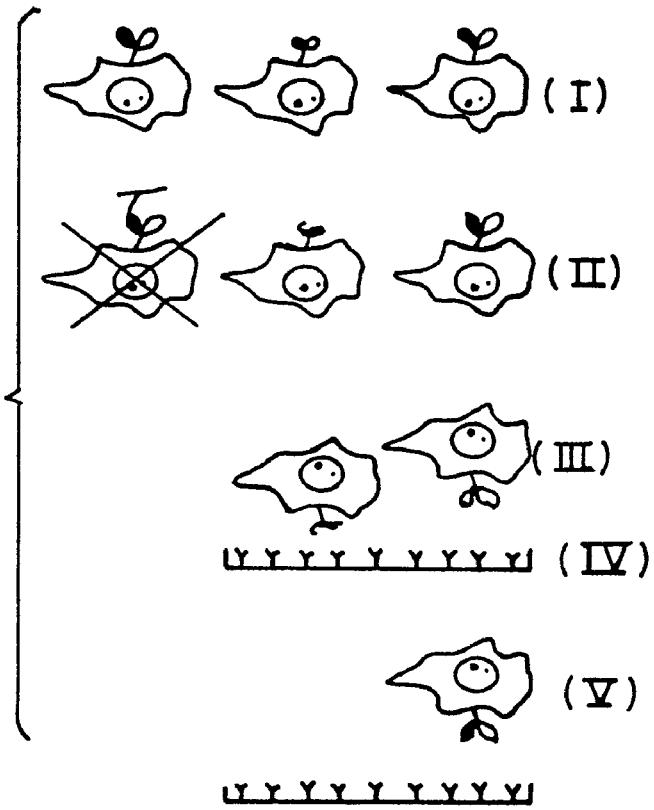

Binding domain loss mutants isolation was carried out as represented in FIG. 1 and as described in Peterson, A. and Seed, B. (Oct. 29, 1987) Nature 329:842–846, incorporated herein by reference. Epitope loss mutants were isolated as follows: COS cells were transfected with a pool of mutagenized plasmids, cultured for 48 hours, harvested and treated sequentially with an anti-CD2 monoclonal antibody (i.e., with a monoclonal antibody recognizing the epitope whose loss is desired), rabbit anti-mouse immunoglobulin antibody and complement. This step is referred to as the negative selection step and is represented as step (i) in FIG. 1B.

Because spontaneous deletion mutants arise frequently in COS cells (Calos, M. P., Proc. Natl. Acad. Sci. USA, 80:3015–3019 (1983); Razzaque, A. et al., Proc. Natl. Acad. Sci. USA, 80:3010–3014 (1983), a positive selection step was carried out as follows: the cells spared by complement treatment were treated with antibody(ies) recognizing a distinct CD2 epitope(s) and allowed to adhere to dishes coated with goat anti-mouse immunoglobulin antibody. Wysocki, L. J. and Sato, V. L., Proc. Natl. Acad. Sci. USA, 75:2844–2848 (1978). Antibodies used for isolation of epitope-loss mutants are shown in Table 1.

Plasmid DNA recovered from the adherent cells (Hirt, B., J. Mol. Biol. 26:365–369 (1967), incorporated herein by reference) was next transformed into E. coli, amplified, and reintroduced into COS cells for further rounds for yield enhancement. At the end of the selection process, DNA from individual bacterial colonies was transfected into COS cells which were then scored for antibody binding.

TABLE 1

| Antibodies Used for Epitope-Loss Mutant Isolation | |
|---|---|
| Antibody | Isotype |
| 9.6 | $IgG_{2a}$ |
| 7E10 | $IgG_{2b}$ |
| MT910 | $IgG_1$ |
| MT110 | $IgG_1$ |
| 95-5-49 | |
| 35.1 | $IgG_{2a}$ |
| T11/3PT2H9 | $IgG_1$ |
| T11/3T4-8B5 | $IgG_{2a}$ |
| 9-2 | IgM |
| Nu-Ter | $IgG_1$ |
| CLB-T11/1 | $IgG_1$ |
| *39B21 | $IgG_{2a}$ |
| Ts1/8.1.1 | $IgG_1$ |
| F92-3A11 | $IgG_1$ |
| 9.1 | $IgG_{2b}$ |
| OCH217 | IgM |

*Antibody 39B21 is a rat monoclonal and all others are mouse antibodies.

The vector piH3M was used for isolation of CD2 mutants. A segment of cDNA encoding for CD2 was inserted into the vector piH3M. As discussed above, piH3M contains a plasmid origin of replication and a suppressor tRNA gene allowing replication and selection in E. coli. In addition, it contains replication origins from bacteriophage M13 and SV40 virus (FIG. 1a). These allow for production of a single-stranded version of the plasmid and for amplification of the plasmid following introduction into cells expressing the proteins necessary for SV40 replication, i.e., COS monkey cells. Expression of cell cDNA surface antigen in COS cells is directed by the immediate early region promoter from the human cytomegalovirus. RNA splicing and 3' end processing signals are found downstream from the cDNA and are derived from SV40 virus.

The initial round of mutant isolation took advantage of the high mutation rate experienced by DNAs transfected into tissue culture cells (Calos, M. P. et al., supra; Razzaque, A. et al., supra; and Miller, J. H. et al., EMBO J. 3:3117–3121 (19840)). A population of plasmids, mutagenized by passage through COS cells was recovered in *E. coli*. The mutagenized pool was subjected to three subsequent rounds of selection using monoclonal antibody (Mab) 9.6 for the negative selection and Mab 35.1 for positive selection, and a single mutant was isolated (FIG. 2).

The initially isolated mutant had two nucleotide substitutions, changing Lys48 to Asn and Asp186 to Glu. Separation of the two changes by oligonucleotide site-directed mutagenesis showed that Lys48Asn was solely responsible for the loss of antibody 9.6 binding. However, further attempts using other antibodies to isolate additional mutants from this pool were unsuccessful.

To increase the likelihood of mutant isolation, the rapid oligonucleotide directed random mutagenesis method described hereinabove was employed. As discussed above, a homogeneous and nonspecific substitution of all possible basepairs encoding the CD2 extracellular domain was created from a collection of 20 overlapping 33-mer oligonucleotides synthesized with a mixture of 95% by mole of the wild-type base at each position and 1.7% by mole of each of the other three bases. The oligonucleotides were overlapped because the residue attached to the matrix during synthesis cannot be conveniently adulterated and because the efficiency of incorporation of mutations falling at the 5' end of the oligonucleotide is not known.

In order to maximize the efficiency of base pair substitutions, the procedure of Kunkel et al., supra, was used to incorporate the mutant oligonucleotides into expression vector piH3MCD2 (FIG. 1*a*). Based on the degree of mutation of the oligonucleotides and the efficiency of their incorporation, it was estimated that approximately 40% of the plasmids resulting form transformation into *E. coli* contained at least one base substitution. Twenty separate mutagenesis reactions were performed and transformed into *E. coli*, and a portion of each resulting culture pooled to form a mutant stock.

When an aliquot of the mutant stock was subjected to the selective regime using Mab 9.6 for negative selection and Mab 35.1 for positive selection, 10–15% of the recovered plasmids were found to bear the desired phenotype. After two rounds, the desired mutants comprised 50–75% of the plasmid population. The same mutant stock was used for all subsequent mutant selections.

Location of CD2 Mutations

The pattern of amino acid substitutions in the mutants defines three distinct regions of the CD2 molecule comprising many sequence variants: antibodies that participate in activation and block erythrocyte adhesion bind to a first region; antibodies that only block adhesion bind to a second region; and antibodies that participate in activation but do not block adhesion bind to a third region.

One-hundred fourteen (114) primary mutants were isolated, resulting in a collection of 50 different amino acid sequence variants. The results of the mutant selections are summarized in FIGS. 2A–2B and 3A–3B. All of the variation falls in three discrete regions. Region 1 is centered about Lys48 and contains 47 mutations for all of the group I antibodies (9.6, 7E10, MT11D and MT91D), all but one of the group II antibodies, and one group III antibody (FIG. 3A). Region 2 is centered about Gly95. In this second epitope region, 27 mutants were obtained using five different antibodies for negative selection (FIG. 3B). The sole stimulatory antibody contacts a wider region than any of the other antibodies, but no other clear distinction can be made; each antibody gives a unique patten of mutation. Most of the antibodies recognizing regions 2 have little effect on T cell activation. Region 3 is represented by a single mutation which causes loss of reactivity with both of the group IV antibodies (9.1 and OCH217).

FIG. 3A in particular shows the mutant collection defining epitope region 1. CD2 residues 42–56 are shown above the amino-acid substitution encoded by each mutant. The first column on the right shows the antibody used for negative selection. The second column shows the positive selection antibody(ies). "All 16" indicates that all 16 monoclonals in Table 1 were combined and used for the positive selection step. "7 others" means that the seven antibodies other than 35.1 recognizing the first epitopic region were combined for the positive selection step. Variants directly under the CD2 sequence were obtained by selecting mutants from a pool of plasmids mutagenized throughout the extracellular domain of the protein. The variants under the bars indicate mutants acquired by the novel method of this invention using plasmids mutagenized only by oligonucleotide directed random mutagenesis covering the span of the bars. The mutant collection defining epitope region 2 is shown in FIG. 3B. CD2 residues 86 through 100 are shown above the mutant substitutions. Other notations are as in FIG. 3A.

Mutant CD2 Erythrocyte Rosetting

The ability of the mutant CD2 proteins to promote LFA-3 mediated adhesion of human erythrocytes to transfected COS cells was measured by a qualitative erythrocyte rosette assay. Three phenotypes were scored; wild-type, partial, and non-rosetting. Many of the mutations leading to changes in region 1 and 2 (reactive with groups I, II and III antibodies) dramatically reduced resetting. To examine this further, a few mutants were created by specific site-directed oligonucleotide missense mutagenesis. Substitution of asparagine or alanine for lysine at each of positions 46, 47, and 48 of epitope region 1 demonstrated a striking correlation between the binding of the group I antibody Mab 9.6 and erythrocyte adhesion. Lys46Asn/Ala showed a modest effect on both Mab 9.6 and erythrocyte binding; Lys47Asn/Ala had no effect on either; and Lys48Asn/Ala completely abolished both interactions. Similarly, residue 51 could be shown to be important for both erythrocyte and Mab 9.6 binding. Residue 52 had only a weak effect on either interaction.

Subsequent experiments with other antibodies and other mutants showed that Lys48 plays a major role in the interaction of CD2 with group I antibodies and LFA-3 (FIGS. 2A–2B and 4). For example, the mutant Lys48Gly is unreactive with all of the group I antibodies, and none of the CD2 molecules substituted at Lys48 has any detectable rosetting activity. The behavior of substitutions at Lys48 constitutes one of the strongest pieces of evidence that group I antibodies mimic the effect of LFA-3 binding in provoking T cell proliferation.

Only one antibody which participates in the activation of T cells recognizes determinants in the second epitopic region. Substitutions in this area characteristically diminish resetting without completely eliminating it, in agreement with the notion that mutations selected with antibodies which promote activation are usually mutations that affect resetting.

Effects of Individual CD2 Amino Acid Substitutions

Although some residues can directly determine antibody reactivity, it appears that others, of secondary importance for antibody affinity, can be identified because they frequently are altered in association with other changes. For example, a Lys46Asn substitution frequently is found in mutants which do not bind Mab 9.6, but by itself causes only partial loss of binding. A similar phenomenon may be present in the repeated isolation of position 51, 52 double mutants.

In principle, amino acid substitutions could lead to loss of antibody or LFA-3 binding by either elimination of a specific interaction or by causing a local denaturation. Some patterns of antibody or LFA-3 binding argue against the latter possibility.

For example, all of the molecules substituted at Lys48 still bind Mab 35.1, which is sensitive to changes at Ile49. Similarly, both Mab 9.6 and LFA-3 cannot bind to the Gln51Leu variant, which nonetheless is recognized by antibodies 7E10 and 9-2. CD2 having a Gln51Arg substitution is unreactive with 7E10 and 9-2 but binds LFA-3 indistinguishably from wild-type. In the second epitope region, the Tyr91Asp mutation causes loss of rosetting, but antibody NU-TER binding is not affected, even though many substitutions at position 92 eliminate NU-TER reactivity.

In one case, local denaturation may play a prominent role in loss of antibody binding. Proline residues are known to have limited conformational freedom, which does not favor alpha helix formation (Chou, P. Y. and Fasman, G. D., Ann. Rev. Biochem. 47:251–276 (1978)). Gln51Pro variants are not recognized by any of the antibodies reacting with the first epitopic region, and Gln51Pro is frequently isolated by negative selection with region 1 antibodies if positive selection with all 16 antibodies is used. In the most extreme case, negative selection with Mab 35.1 leads exclusively to Gln51Pro when all 16 antibodies are combined for positive selection. To avoid repetitive isolation of Gln51Pro, many of the mutants in the first epitopic region (FIGS. 2A–2B and 3A–3B) were isolated using Mab 35.1 as the sole positive selection antibody.

To isolate a 35.1 mutant other than Gln51Pro, only the antibodies which fail to bind to this variant were used for positive selection. After three cycles of enrichment, a single 35.1 Ile49Gln mutant was obtained which was altered in all three bases of the original codon. The unusual nature of this mutation suggests that the 35.1 antibody derives its affinity from multiple features of the CD2 conformation, so that substitution for a single feature only rarely leads to greatly lowered affinity. The Gln51Pro mutation may eliminate several of these interactions by gross alteration of the local secondary structure. Because the affinity of the 35.1 antibody is comparable to that of antibody 9.6 (Martin, P. J. et al., J. Immunol. 13:180–185 (1983)), it appears that the unusual mutational spectrum of this antibody arises from a qualitatively different mode of binding and not simply a stronger interaction. Another group II antibody, T11/3PT2H9, also gave Gln51Pro mutations exclusively when all 16 monoclonals were pooled for the positive selection step.

CD2 Group IV Antibody Epitope

Only one mutant was obtained for the group IV antibodies, a Tyr140Asn/Gln141His double substitution. However, group IV antibodies react only weakly with the CD2 molecule expressed on COS cells, a situation reminiscent of the weak reactivity of group IV antibodies with CD2 on unactivated T cells, (Meuer, S. C., et al., Cell (1984) 36:897–906). Prior activation of T cells or incubation with a group I antibody is necessary to make the group IV antibody epitope available (Meuer, S. C. et al., supra). The rapid acquisition of group IV antibody reactivity suggests that it is caused by a conformational change in the molecule and not by de novo synthesis of a different species (Meuer, S. C. et al., supra; Yang, S. Y. et al., J. Immunol. 137:1097–1000 (1986).

Each of the monoclonal antibodies in this study gave a contiguous linear pattern of mutational variation. All three epitopic regions are hydrophilic as would be expected for an exposed portion of the molecule available for antibody binding (FIG. 2B). Several alternatives may be put forth to explain why only a few restricted portions of the molecule give rise to multiple independent antibodies. For example, a portion of the first epitope is predicted to form an alpha helix with hydrophilic residues on one side of the helix and hydrophobic residues on the other (Chou, P. Y. and Fasman, G. D. (1978) Ann. Rev. Biochem. 47:251–276). Such a helix is thought to form a particularly favored antigen for T cell recognition (De Lisi, C. and Berzofsky, J. A. (1985) Proc. Natl. Acad. Sci. USA 82:7048), and recognition of this region by mouse helper T cells may focus the antibody response. In the region corresponding to epitope region 2 (FIG. 3b), three potential N-linked glycosylation sites are found in the rat CD2 sequence (Williams, A. F. et al. (1987) J. Exp. Med. 165:368–380) which are not present in the human sequence. This may serve to enhance reactivity with the human sequence by reducing the number of mouse suppressor T cells which might cross-react with the human sequence. Alternatively, the restricted spectrum of antibody binding sites may arise from the prior selection of antibodies for erythrocyte receptor reactivity.

HIV Binding Site and Epitope Mapping for CD4

The method of the present invention has been used to isolate amino acid substitution variants of CD4 (see Peterson, A. and Seed, B. (Jul. 1, 1988) Cell 54:65–72, incorporated herein by reference). Mutations which affect binding of HIV are found in an epitope cluster which includes the Leu3a epitope (FIG. 4). The epitope mapping experiments show that most anti-CD4 antibodies, including those which are most effective at blocking CD4-gp120 interactions, recognize the amino-terminal domain of CD4. The locations of epitopes together with the similarity between the amino-terminal domain of CD4 and immunoglobulin V domains allows modelling of the surface of CD4 which interacts with gp120.

CD4 may mediate both cell—cell adhesion and antigen-independent activation reactions. The HIV envelope protein gp120 binds to CD4 with high affinity (Kd $10^{-9}$M), allowing entry of the virus into the host cell. Cell surface expression of CD4 is necessary for viral penetration and appears, in human cells, to be sufficient for susceptibility to infection. Interaction between CD4 and gp120 also mediates syncytium formation, between infected cells and uninfected cells bearing CD4, which is at least partly responsible for the cytopathic effects observed following viral infection in vitro.

The functionally-defined binding sites identified by the method of this invention, and in particular those directed to the CD2 molecule or the CD4 molecule, can be prepared in soluble form and may therefore be used in immunodiagnostic assay methods well-known in the art, including radioimmunoassays, enzyme immunoassays and enzyme-linked immunosorbent assays. Moreover, protein binding domains isolated by the method of the present invention can be prepared in soluble form and administered alone or in combination with other soluble binding domains for the treatment of immune-related disorders in animals, including humans. Examples of such conditions are immune deficiency diseases, AIDS, asthma, rheumatoid arthritis, immunopathogenic renal injury, immune endocrinopathies, and tissue/organ transplant rejection.

Soluble forms of CD4, lacking the third disulfide bonded extracellular domain as well as the transmembrane and cytoplasmic regions, are able to bind gp120. Deen, K. C. et al. (1988) Nature 331:82–84; Dalgleish, et al. (Nov. 7, 1987) The Lancet, pp. 1047–1049. This limits the HIV binding activity of CD4 to the two most amino terminal domains. The most amino terminal domain has a great deal of homology to immunoglobulin V region domains, suggesting that gp120 may interact with an immunoglobulin-like domain of CD4.

The binding site for HIV on CD4 has been indirectly localized by using monoclonal antibodies to interfere with CD4-gp120 interactions. Two epitopes of CD4 seem to be near the HIV binding site, one defined by the Leu3a and OKT4A antibodies and the other defined by the MT151 and VIT4 antibodies. The two epitopes are spatially distinct; antibodies recognizing one epitope do not interfere with binding of antibodies recognizing the other. Anti-idiotype antibodies raised against the Leu3a antibody also recognize a conserved portion of gp120 indicating that the Leu3a epitope may actually comprise part of the HIV binding site.

Thus, as a result of identification of the HIV binding site on CD4, it is possible to produce peptides which interfere with the ability of HIV to infect human cells by preventing the virus from interacting with the CD4 cell surface receptor. This can be done, for example, by producing peptides which bind to the HIV, thus preventing it from binding to the cell surface receptor. Particularly useful, for example for this purpose, is a peptide having the same, or an essentially homologous, amino acid sequence as the Leu3a epitope, or that overlined in FIG. 4. Such a peptide can be synthesized, using known techniques, and introduced (e.g., by intravenous administration) into an individual in soluble form (e.g., as part of another protein, such as an immunoglobulin) in sufficient quantities to bind with the HIV and interfere with its ability to infect cells.

By "essentially homologous" is meant an amino acid sequence having at least about 90% sequence identity to the amino acid sequence determined by the present invention to be the binding domain for a ligand, and retaining substantially the same affinity to the ligand as the native or wild type binding domain. Binding affinity can be determined by methods known in the art, such as by Scatchard analysis.

When used for immunotherapy, the peptides of the present invention can be labeled or unlabeled with a therapeutic agent. Examples of such agents include drugs, radioisotopes, lectins, and cell toxins. Methods and compositions of this invention will be further exemplified by the following, nonlimiting examples.

EXAMPLES

Example I

CD2 Oligonucleotide Mutagenesis

Mutant oligonucleotides were synthesized on an Applied Biosystems DNA synthesizer using a mixture of phosphoramidites, 95% of the wild-type sequence and 1.7% of each of the other three phosphoramidites, at each position. The 600 nucleotides of CD2 sequence following position 63 as it appears in Seed, B. and Aruffo, A. (1987) Proc. Natl. Acad. Sci. USA 84:3365–3369, were synthesized in a collection of twenty 33-mer oligonucleotides. The sequence also appears in Applicants' U.S. Pat. No. 5,506,126. Each oligonucleotide overlaps with the preceding oligonucleotide sequence by three bases. The 3' most base is immutable (the synthesis proceeds 3'–5' from a resin fixed phosphoramidites); however, mutants can be obtained that are altered in the 5'-most base determined by an oligonucleotide. This would imply that an overlap of 1 base is sufficient to make all positions mutable. The oligonucleotides were not further purified following deprotection and desalting, but were immediately phosphorylated using polynucleotide kinase (Pharmacia) under the conditions described by Maniatis, T. et al. (1982) *Molecular Cloning: A Laboratory Manual*, Cold Spring Harbor Laboratory, Cold Spring Harbor, N.Y. Ten nanograms of each phosphorylated oligonucleotide were separately added to 500 ng of single-stranded cDNA template (synthesis described below). Each mixture was heated to 70° C. briefly, cooled to room temperature, and deoxynucleotide triphosphates, 10 units of reverse transcriptase (Life Sciences) and reverse transcriptase buffer were added to make a final reaction volume of 10 μl. After a one-hour incubation at 37° C., ATP, dithiotreitol and bovine serum albumin were added to approximate the recommended reaction conditions for T4 DNA ligase (New England Biolabs) which was added (400 units) for an additional 15-minute incubation at 37° C. One-fifth of each ligation reaction was used to transform *E. coli* resulting in approximately 1,000 bacterial colonies from each oligonucleotide. The colonies from each plate were scraped into LB and 20 glycerol stocks were made, each representing a population of piH3MCD2 mutagenized within a different 33 base pair sequence.

Single-stranded template DNA was prepared in *E. coli* strain BW313/p3, derived from BW313 (Kunkel, T. A. (1985) Proc. Natl. Acad. Sci. 82:488–492 by transformation with the RP1-related plasmid p3 (Seed, B. (1983) Nucl. Acids Res. 11:2427–2445). BW313/p3 allows selection of plasmids containing an amber suppressor tRNA gene by growth in media containing ampicillin and tetracycline. The plasmid piH3MCD2, which contains SupF was introduced into BW313/p3, and single-stranded DNA was prepared by infecting the plasmid-carrying strain with wild-type M13 virus as described (Levinson, A. et al., (1984) J. Mol. Appl. Genetics 2:507–517). The single-stranded DNA produced in BW313/p3 has 20–30 uracil residues per template. This allows efficient selection for the DNA strand made in vitro and, thus, for incorporation of the oligonucleotide (Kunkel, T. A. supra). Incorporation frequency was approximately 75%.

Specific amino acid changes at positions 46, 47 and 48 were made in a similar fashion, except that oligonucleotides with specified coding potential were used instead of random mutant oligonucleotides.

Example II

CD2 Mutant Selection

Spheroplasts were prepared from bacteria harboring mutagenized piH3MCD2 and fused to COS cells as described in Applicants' U.S. Pat. No. 5,506,126. Forty-eight hours following fusion, the COS cells expressing CD2 were detached from the dish in PBS/1 mM EDTA. The COS cells from six 60-mm dishes were then incubated in PBS, 10% calf serum, 0.02% sodium azide (PBS-FBS) containing a 1/1000 dilution of ascites fluid of the negative selection antibody. All antibody incubations were performed in 1 ml of PBS-FBS for 30 minutes on ice and were followed by centrifugation through a cushion of 2% Ficoll in PBS. The cells were then incubated with 5 ug/ml rabbit antimouse Ig antibody (Rockland). Two mls of 50% rabbit complement (Pel-Freeze) in DME (GIBCO) were then added and incubated at 37° C. for 30 minutes with agitation to prevent clumping. The complement was removed by dilution to 10 mls with PBS/5 mM EDTA and subsequent centrifugation of the cells through a 5 ml ficoll cushion. The cells were then incubated with a 1/1000 dilution of the positive selection antibody and added to sheep antimouse immunoglobulin (Cooper Biomedical) coated dishes (Wysocki, L. G. and Sato, V. L. (1978) Proc. Natl. Acad. Sci. USA 75:2844–2848) prepared as described in Applicants' U.S. Pat. No. 5,506,126. After allowing an hour for the cells to attach, the nonadherent cells were gently washed away, and DNA was prepared from a Hirt supernatant of the adherent cells. The recovered DNA was transformed into *E. coli* MC1061/p3, and the resultant colonies were either subjected to further rounds of selections, or analyzed directly. For direct analysis, plasmid DNA prepared from individual colonies was used to transfect COS cells by a DEAE dextran procedure as described in Applicants' U.S. Pat. No. 5,506, 126. The mutant phenotypes were assayed by sequential indirect immunofluorescence using first the negative selection antibody followed by the positive selection antibody.

When the total extracellular domain of CD2 was to be mutagenized, bacteria from all 20 pools were combined to give a randomly substituted preparation. For directed mutation, the bacteria from only one or two pools was used.

A partial panel of monoclonal antibodies was obtained through the Third International Workshop on Leukocyte Typing.

Example III

DNA Sequence Analysis and Rosetting of CD2 Mutants

The DNA sequence of the mutants was determined on single-stranded templates or alkali denatured plasmid DNA by the dideoxynucleotide method (Sanger, F. et al. (1977) Proc. Natl. Acad. Sci. USA 74:5463–5467). For mutants obtained using randomly mutated piH3MCD2, the entire extracellular domain of CD2 was sequenced. For mutants obtained by oligonucleotide directed random mutagenesis a 200 bp portion of the cDNA containing the mutated region was sequenced. In all cases the mutations fell within the span of a single oligonucleotide, as expected.

Forty-eight hours after transfection, a 2% suspension of Peterson erythrocytes was allowed to settle onto adherent COS cells for one-half hour at room temperature. Excess erythrocytes were gently removed and the phenotype was scored by microscopic inspection. All rosette phenotypes were assayed on at least three separate occasions with wild-type and negative controls. In some instances, expression of surface CD2 was confirmed by indirect immunofluorescence following exposure to erythrocytes.

Wild-type rosettes are characterized by tight binding of erythrocytes to the COS cells. Partial rosetting has fewer erythrocytes more loosely bound than do wild-type rosettes. Lack of rosetting means that the mutant is indistinguishable from a negative control (i.e., CS8—Expressing COS cells). Table 2 summarizes the various mutant substitutions giving rise to rosette patterns. Amino acid substitutions separated by commas are present on the same molecule.

TABLE 2

| Wild-Type Rosette | Partial Rosette | No Rosette |
| --- | --- | --- |
| Lys47Ala/Asn | Lys46Ala/Asn | Lys48Ala/Met/Glu |
| Gln51Arg | GlnPhe51-2ArgSer | Gln51Leu |
|  | Phe52Val,Glu55Gly | Gln51Pro |
| TyrGln140-1AsnHis | Tyr91Asp | Thr93Ser,Gly95,Val |
|  | Asp92His | Asn97Ile |

Example IV

CD4 Mutant Selection

The general method described herein, by which surface antigen epitope loss mutants are isolated, has been applied to the CD4 antigen with the modification that spheroplasts were prepared from bacteria harboring mutagenized plasmid piH3MCD4. The CD4 antigen is of particular interest because it serves as the T-cell binding site for HIV.

Isolation of epitope loss mutants was carried out as follows: A CD4 cDNA isolated from the HPB-ALL cell line was mutagenized by annealing mutant oligonucleotides, prepared as described in Example 1, to a deoxyuridine substituted single-stranded template. The mutagenized population of plasmids was introduced into COS cells by spheroplast fusion. Two days after fusion, the cells were harvested and sequentially incubated with an anti-CD4 monoclonal antibody, rabbit anti-mouse Ig antisera and rabbit complement. This resulted in selection against the cells bearing determinants recognized by the monoclonal antibody. In order to avoid the isolation of rearrangements which completely eliminate CD4 expression, the cells which remained after complement lysis were incubated with pooled anti-CD4 monoclonals and the cells were allowed to adhere to goat anti-mouse Ig coated petri dishes. Plasmid DNA recovered from cells adhering to the antibody coated plates was used to transform *E. coli*, amplified, and reintroduced into COS cells. After three rounds of selection in COS cells, plasmid preparations from individual bacterial colonies were transfected into COS cells and assayed two days later by indirect immunofluorescence. Plasmids which encoded CD4 molecules that failed to react with the monoclonal used for complement fixation but which retained other CD4 determinants were then sequenced. FIGS. 4-1 and 4-2 show the primary sequence locations of amino acid whose replacement leads to loss of binding the indicated antibodies. Table 3 indicates the amino acid which is substituted in each case. The amino acid variants are referred to by a wild type residue-position-new residue convention in Table 3 and throughout the subject application.

Most of the mutations which were isolated were nucleotide substitutions. An insertion and a deletion were also isolated. These two rearrangements are apparently unrelated to the oligonucleotide mutagenesis but instead result from passage through COS cells. It is known that transfection of COS cells results in a mutation rate of about 1%. The majority of the lesions are insertions and deletions.

CD4 Epitope Locations

Most of the mutants, including several selected using antibodies which can potently block gp120-CD4 interaction, encode amino acid substitutions in the amino-terminal, Ig V related, domain of CD4. This domain has several of the cardinal features of an Ig domain, two cysteines, an arginine and a glutamic acid, which in an immunoglobulin form a disulfide bond and a salt bridge respectively and a conserved tryptophan residue, making it extremely likely that the amino-terminus of CD4 folds in the same fashion as an Ig V domain. Based on the hypothesis that this domain of CD4 does fold in a fashion resembling an Ig V domain, a model of the locations of the amino acid substitutions in a folded structure can be made. Modelling allows predictions about gp120 interaction with this domain of CD4 to be made.

The 66.1 antibody selects mutations causing amino acid variation of the amino terminus of CD4 (FIG. 4-1 and Table 3). The substitutions are separated by up to 23 residues, suggesting that 66.1 recognizes an epitope which is formed by the three-dimensional folding pattern of the protein and not by the primary amino acid sequence. The mutations fall into two regions which would correspond to the first and second hypervariable regions of an Ig V segment. These two regions are near each other in a folded immunoglobulin although they are fairly distant in the primary sequence. This result strongly supports the idea that the amino terminal domain of CD4 folds in a similar fashion to Ig V domains.

The ability of anti-CD4 antibodies to block the binding of other anti-CD4 antibodies also supports the concept of an Ig V domain folding pattern. For example, the mutants selected using the VIT4 and 13B.8.2 antibodies encode amino acid substitutions separated by about 70 residues from those encoded by G19-2 selected mutants. Both 13B.8.2 and VIT4 can substantially block the binding of G19-2; this would be predicted from the Ig folding pattern.

The 66.1 and G19-2 antibodies are unable to block CD4-gp120 interaction even at many times the saturating concentration. This means that gp120 interacts with CD4 in a fashion that does not involve the face of the molecule which would be formed by the B and C strand homologs of CD4. Binding of either Leu3a or OKT4A can completely block binding of the other antibody. Neither antibody's binding is able to effectively eliminate binding of the 66.1 and g19-2 antibodies. The mutant selected using OKT4A encodes a substitution for a residue in the D strand of an Ig fold; the Leu3a selected mutants encode variants of the C' and C" strands. The configuration of the B, C, C', C" and D strands in an Ig fold leads to the prediction that Leu3a and OKT4A interacts with the face of the domain formed by the D, E and C" strands homologs of CD4. Both OKT4A and Leu3a block CD4-gp120 interaction at very low antibody concentration. If OKT4A and Leu3a block access of gp120 to a site on the amino terminal domain of CD4, the site must be on the D, E and C" strand homologous regions of CD4.

Binding of the VIT4 antibody to CD4 does not interfere with the binding of either Leu3a or OKT4A. This is not surprising given the VIT4 epitope location. However, VIT4 is as potent as Leu3a and OKT4A at blocking CD4-gp120 dependent syncytium formation. VIT4 might indirectly block access of gp120 to a binding site on the D, E, C" strand or might interfere with a spatially distinct binding site, either by blocking access indirectly or by occupying the binding site. The fact that G19-2 competes with VIT4 for binding to CD4 but does not block CD4-gp120 interaction suggests that the ability of VIT4 to block gp120 is indirect. Phylogenetic conservation of HIV susceptibility without conservation of the VIT4 epitope supports the notion that this epitope is not directly involved in HIV binding.

The Mt151 antibody blocks interactions with CD4 in a similar fashion to VIT4; it blocks gp120 interaction but not OKT4A or Leu3a binding. The substitutions encoded by Mt151 epitope loss mutants are found 5 residues and 77 residues carboxy terminal to the VIT4 epitope loss-associated substitution. The MT151 antibody clearly recognizes an epitope formed by the conformation of the folded protein. This epitope overlaps with the VIT4 and 13B.8.2 epitope region but also includes the carboxy terminal part of the second domain. The MT151 epitope places the carboxy terminus of the second disulfide bonded domain of CD4 in close proximity to the carboxy terminus of the amino terminal Ig-like domain and strengthens the possibility that VIT4 and Mt151 block CD4-gp120 interaction by blocking access to a site on the second domain, not the first domain.

Effect of CD4 Mutations on Syncytium Formation

The mutants allow some of the predictions made from the epitope locations to be tested. One manifestation of CD4-gp120 interaction is the formation of multinucleate, giant cells. These syncytia are at least partly responsible for the cytopathic effects of viral infection. Syncytia can be formed by cells expressing only the HIV env gene product gp160 interacting with cells expressing CD4. We were unable to induce syncytia in transfected COS cells; however, HeLa cells proved to be very effective at cell—cell fusion. The mutants were each tested for their ability to collaborate in syncytia formation, by transfection of HeLa cells, followed by infection with a vaccinia virus recombinant which expresses HIV gp160. HeLa cell lines which stably express some of the CD4 mutants were created using a retroviral vector which carries G-418 resistance. Single clones or pooled, G-418 resistant cells were expanded and tested for syncytium formation following infection with a vaccinia virus expressing gp160. The same results were obtained with the transient assay, stably expressing clones or pooled G-418 cell lines.

Most of the amino acid variants were as effective as wild-type CD4 in supporting syncytia formation. In contrast, replacements of amino acids 39, 44, 45 and 46 had a striking effect on the ability of CD4 to induce syncytia as did the insertion mutation which was isolated using MT151 selection. Several of the substitutions seemed likely to cause a local denaturation of the protein. For example, the variant selected using the T4/18T3A9 antibody had a proline replacing the glutamine normally found at position 39. Proline has a much more constrained backbone than glutamine and might be expected to alter the local folding structure. Similarly, the variants selected using OKT4D, Gly46Arg and Gly46Glu, replace glycine with bulky, charged residues and might denature the C" strand homolog of CD4.

Although the substitutions which affect syncytium formation may disrupt protein folding, several observations suggest that the effects on syncytium formation are due to short range changes in the protein structure. Substitutions, similar to those which eliminate CD4 mediated syncytium formation, when at other locations, do not have the same effect; the Gln39Pro variant has only a moderately reduced ability to support syncytium formation, the Gly37Glu and Gln164Pro variants are as effective as wild-type CD4 in participating in syncytium formation. The Lys45Asn, Gly46Val double-substitution variant selected using Leu3a is not obviously disruptive but does eliminate syncytium formation.

The effect of the insertion mutation, isolated using MT151, on the structure of CD4 is hard to assess. It results in a large insertion, 13 amino acids, near the end of the second domain. The point mutations selected using MT151 demonstrate that CD4 folds in a fashion such that this portion of the second domain is very close to the carboxy terminus of the first domain. It is possible that the insertion has very indirect effects on CD4 folding and alters the first domain.

Mutations which disrupt syncytia formation could be of at least two classes. It seems certain that mutations which eliminated the ability of CD4 to bind gp120 would eliminate the ability to induce syncytia formation. Another class of mutation is also possible; mutations which eliminate syncytia formation but not binding.

Effect of CD4 Mutations on HIV Binding

The effect of the mutations on the ability of CD4 to bind HIV was assessed using an indirect immunofluorescence assay. Concentrated virus particles were incubated with COS cells expressing the different mutants and bound particles were detected using human sera with a high anti-gp120 titer. Binding was quantitated by analysis of cells on a cytofluorometer. In each case, the expression of CD4 on the cell surface was quantitated in parallel using anti-CD4 monoclonals and indirect immunofluorescence. The ability of the variant CD4 molecules to bind virus was consistent with their relative effectiveness in syncytia induction. The mutations which eliminated syncytia formation also eliminated binding of virus particles. Mutations which profoundly reduced the ability of CD4 to support cell fusion likewise reduced their ability to bind gp120. This shows that the primary effect of the mutations is on the ability of CD4 to bind gp120 and not on their ability to induce syncytia.

The effects of the various mutations on the ability of CD4 to bind gp120 are largely consistent with the predictions made from the epitope locations. Mutations which are likely to disrupt the C' strand have altered behavior in binding and syncytia formation assays. Mutations which alter the C" strand eliminate the ability of CD4 to bind virus. The mutant selected using the OKT4A antibody might have been expected to behave differently from wild-type CD4 in the syncytia formation assay. This mutant encodes an amino acid replacement in the D strand homologous region of the CD4 cDNA. The substitution encoded by the mutant alters a sequence pattern which is conserved between mouse, rat and human CD4 (mouse-SKKG, rat-SRKN, human-SRRS, OKT4A-SRRR). It seems likely that this amino acid replacement would alter the predicted D strand of CD4; however, it does not alter the binding of HIV. In addition, the OKT4A epitope is poorly conserved in primate species which are infectable by HIV, suggesting again that the ability of OKT4A to block HIV binding is indirect, presumably by blocking access to the Leu3a epitope region.

The VIT4 epitope is also not as well conserved as HIV infectability in primate species and the mutation selected using this antibody does not affect HIV binding. VIT4 probably also blocks HIV binding by indirectly preventing gp120 from interacting with sequences distinct from the antibody recognition site. The mutations selected using this antibody fall in what would correspond to the fourth hypervariable region of an Ig V domain. It is possible that VIT4 blocks access to that portion of the HIV binding site which we have identified as the Leu3a epitope. Such an explanation is not obvious from the proposed relationship between the two epitope regions and from the fact that VIT4 does not interfere with the binding of Leu3a and OKT4A. The MT151 epitope, which overlaps the VIT4 epitope on the first domain, also reaches the carboxy terminus of the second domain. This epitope connects the VIT4 epitope region more closely to the second domain than to the D, E, C" face of the first domain. The ability of VIT4 and MT151 to block gp120-CD4 interaction therefore raises the possibility of a second domain HIV interaction site.

Anti-idiotype antisera which recognize the Leu3a antibody are able to neutralize diverse isolates of HIV. This led to the suggestion that this antibody must recognize an important determinant of the HIV binding site. The concordance between expression of the Leu3a epitope and susceptibility to HIV in primate species supports the importance of the Leu3a epitope to HIV binding. Direct evidence of identity between the recognition site for Leu3a and a site which is important for the binding of HIV is provided. CD4 variants which are altered in recognition by Leu3a are also altered in their ability to bind HIV. The Leu3a epitope resides on the segment of CD4 which would correspond to the C' and C" strands of an Ig V domain. It may be possible to design reagents which mimic the structure of this portion of the CD4 molecule. Short peptides which comprise the C" strand and its flanking regions might bind to gp120 with sufficient avidity to prevent gp120 interaction with CD4. Replacement of the C' and C" strand of an authentic Ig V region with the CD4 cognates might similarly result in a structure which could interfere with HIV replication and/or pathology. Such reagents would be important therapeutic agents in the treatment of AIDS.

The primary amino acid sequence of the human CD4 protein is shown in FIGS. 4-1 and 4-2. The sequence shown below this represents the mouse sequence where it differs from the human sequence. The underlining indicates the extent of the transmembrane domain of CD4. The bar above the sequence represents the proposed HIV binding site of the CD4 protein. The 16 different antibodies used in the positive selection step are shown along the left-hand margin. The * symbol above the primary sequence indicates that a mutant isolated using a particular antibody has a substitution at that position. Substitutions at amino acid positions 39 and 46 will affect HIV binding. These positions are also indicated in FIG. 4-1. Table 3 presents a summary of the antibodies used in the negative selection step and of the CD4 mutant collection isolated using the methods of this invention.

TABLE 3

| Antibody used for negative selection | | Amino acid replacement (indicated by normal residue-position-new residue) |
|---|---|---|
| Leu3a | K34E* | Lys34Glu |
| Leu3a | N38K and G46D | Asn38Lys and Gly46Asp |
| Leu3a | Q39P and T44S | Gln39Pro and Thr44Ser |
| Leu3a | K45N and G46V | Lys45Asn and Gly46Val |
| T4 | P47S | Pro47Ser |
| 94b1 | T44P | Thr44Pro |
| OKTD | G46D | Gly46Asp |
| OKT4D | G46R | Gly46Arg |
| T4/18T3A9 | Q39P | Gln39Pro |
| F101-5 | G37E | Gly37Glu |
| G19-2 | S18Y | Ser18Tyr |
| G19-2 | Q19K | Gln19Lys |
| 66.1 | Q19H and H26R | Gln 19His and His26Arg |
| 66.1 | S22G and I23V and H26L | Ser22Gly and Ile23Val and His26Leu |
| 13B.8.2 | E76K | Glu76Lys |
| VIT4 | Q78L | Gln78Leu |
| OKT4A | S59R | Ser59Arg |
| BL/10T4 | G110A | Gly110Ala |
| BL/10T4 | P121H | Pro121His |
| OKT4E | P121H | Pro121His |
| OKT4B | Q164P | Gln164Pro |
| NUTH-1 | A216G | Ala216Gly |
| MT321 | V325I | Val325Ile |

*Single letter codes for amino acids are used in this column.

Example V

Selection of Binding Domain Loss Mutants Using Epstein Barr Virus Derivative Plasmids Expressed in HeLa Cells PiH3M plasmid containing mutant cDNA inserts are synthesized by oligonucleotide directed random mutagenesis as described in Example I. Alternatively, the entire piH3M/cDNA construct can be mutagenized by radiation, chemical mutagens or any other known method. The piH3M/cDNA constructs are then linearized at any restriction site in the SV40, piVX origin, M13 origin or SupF regions such as, for example, the BamHI site located between the polyA and SV40 origin, and inserted into an EBV derivative plasmid as described below. Because the cytomegalovirus enhancer, HIV promoter sequence and SV40 splice and polyA domains remain intact, the inserted linearized piH3M/cDNA can function as an expression cassette.

To ready plasmid p205 of Yates et al. (1985), supra, for insertion of the expression cassette, a polylinker, such as the 421 bp FnuDII fragment of pUC18 containing the lac Z α complementation fragment, is inserted into the MstI site of p205 which corresponds to position 1452 of pBR322. The linearized piH3M/cDNA is ligated into the p205. The resulting derivative, p205/piH3M/cDNA, is then used to transfect HeLa cells, which are then cultured to express the cDNA of interest. The cDNA is expressed from the human cytomegalovirus promoter of the expression cassette. The negative and positive selection steps are then carried out to select transfectants expressing cDNA encoding epitope or binding domain loss mutants. Plasmids are recovered using the Hirt et al., supra, method. The plasmids are then amplified in $E.$ $coli$. The ampicillin resistance gene is available for selection of transformed $E.$ $coli$. The hygromycin gene is available for selection of transformed/transfected expression host cells. Additional rounds of positive and negative selection followed by amplification can be carried out to increase the yield of binding domain loss mutants. Optionally, the plasmids are recovered from $E.$ $coli$, transfected into HeLa cells and scored for binding to negative and positive selection antibodies or ligands. The plasmids are recovered by the Hirt et al. method and mutant cDNAs are sequenced to identify the mutations that cause loss of binding capacity to the negative selection agent.

The use of EBV derivative plasmids can be used to isolate both cell surface and intracellular binding domain loss mutants. In the case of intracellular binding domain loss mutants, the selection steps are carried out by treatment of the HeLa cells to render them porous, followed by treatment with fluorescence-labeled ligands and sorting of mutant cDNAs expressing cells by fluorescence activated cell sorting (FACS). The cells are fixed and permeabilized by methods known in the art such as, e.g., treatment with 4% (v/v) formaldehyde in a nonionic aqueous detergent such as NP40 Triton X100. Alternatively, the cells can be fixed and permeabilized by placing the cells in a −20° C. mixture of 7 parts methanol to 3 parts acetone (v/v). The cells are then treated with the negative selection agent, e.g., fluorescence-labeled ligand to the first binding site, followed by treatment with the positive selection agent, e.g., fluorescence-labeled ligand to the second binding site. FACS is then used to recover cells which demonstrate only the second fluorescence label. Suitable dye pairs useful as the first and second labels are selected to improve sorting efficiency. Suitable dye pairs are, e.g., fluorescein and rhodamine or fluorescein and cycloerythrin.

In the case of cell surface mutant proteins, the selection steps can be carried out either by the subject panning method or by FACS. In the panning method, the HeLa cells are treated with the negative selection ligand, followed by treatment with complement; next, the unlysed cells are treated with positive selection ligand; then the positive selection ligand-cell complexes are recovered by panning with anti-sera coated support. Selection of host cells expressing mutant cell surface proteins by FACS is carried out as described above for intracellular proteins, with the exception that the cells are not fixed and permeabilized prior to treatment with negative and positive selection agents.

Example VI

Selection of Binding Domain Loss Mutants Using Bovine Papilloma Virus Derivative Plasmids Expressed in Murine Cells PiH3M plasmid containing mutant cDNA inserts are synthesized by oligonucleotide directed mutagenesis as described in Example I. Alternatively, the entire piH3M/cDNA construct can be mutagenized by radiation, chemical mutagens or any other known method. As in Example V, the piH3M/cDNA constructs are then linearized at any restriction site in the SV40, piVX origin, M13 origin or SupF regions, such as, for example, the BamHI site located between the polyA and SV40 origin, and inserted as an expression cassette into an BPV derivative plasmid as described below.

The pBPV-H11 plasmid of DiMaio et al. (1982), supra, is linearized at the HindIII site. See FIG. 1 of DiMaio et al. A polylinker that is compatible with the linearized piH3M/cDNA restriction site ends is constructed on the pBPV-H11 HindIII site. The linearized piH3M/cDNA is ligated into the pBPV-H11. The resulting derivative, pBPV-H11/piH3M/cDNA, is then used to transfect C127 cells, which are then cultured to express the cDNA of interest. As discussed above, the negative and positive selection steps are then carried out to select transfectants expressing cDNA encoding binding domain loss mutants. Plasmids are recovered using the Hirt et al. (supra) method. The plasmids are amplified in *E. coli* and ampicillin resistance is used for selection of transformed *E. coli*. Additional rounds of positive and negative selection followed by amplification can be carried out as desired. Optionally, the plasmids are recovered from *E. coli*, transfected into C127 cells and scored for binding to negative and positive selection antibodies or ligands. The plasmids are recovered and mutant cDNAs are sequenced to identify mutations that cause loss of binding capacity to negative selection agent.

As in Example V, BPV derivative plasmids can be used to identify binding domain loss mutants in both intracellular and cell surface proteins.

Example VII

Selection of Binding Domain Loss Mutants Using Yeast 2 $\mu$ Derivative Plasmids Expressed in *S. cerevisiae* cells Mutant piH3M/cDNA plasmids are digested with a restriction enzyme to release the double stranded mutant cDNA. Compatible linkers are ligated to the mutant cDNA for insertion into pAAH5 HindIII site located immediately 3' of the ADC1 (alcohol dehydrogenase) promoter. See Ammerer, G. (1983), supra. The pAAH5 plasmid is designed to contain the polyadenylation and transcription-termination signals of the ADC1 gene downstream of the HindIII linker. The plasmid is transfected into *S. cerevisiae* cells which are then cultured to express the mutant cDNA. The plasmid contains the 2 $\mu$ yeast replicon which allows it to be propagated in *S. cerevisiae*. The cDNA is expressed from the ADC1 promoter.

The negative and positive selection steps are then carried out to select transfectants expressing cDNA encoding binding domain loss mutants. To sort cells according to intracellular proteins having desired binding domain loss mutants, the cells are fixed and permeabilized with 4% paraformaldehyde in an aqueous nonionic detergent such as NP40 Triton X100. The cells can alternatively be fixed and permeabilized by a −20° C. mixture of methanol and acetone (7:3 v/v). The fixed, permeabilized cells are then treated with the negative selection agent and the positive selection agent, and FACS is used to recover those cells which demonstrate binding only to the positive selection agent.

Plasmids are recovered from the selected cells using the Hirt et al., supra, method. The plasmids are amplified in *E. coli*, which are selected by ampicillin resistance. Additional rounds of positive and negative selection followed by amplification can be carried out as desired. The plasmids are recovered and mutant cDNAs are sequenced to identify mutations that cause loss of capacity to bind to negative selection antibody or ligand.

Example VIII

Selection of Binding Domain Loss Mutants Using Bacillus Plasmids

Mutant piH3M/cDNA plasmids are digested with a restriction enzyme to release the double stranded mutant cDNA. Compatible linkers are ligated to the mutant cDNA for insertion into pPL608 (see Williams, D. M. et al. (1981), supra). The mutant cDNA is then ligated into pPL608 at the PstI site and the plasmid is transformed and expressed in *B. subtilis*. As reported by Williams et al., supra, expression of the heterologous cDNA is chloramphenicol inducible.

Because Bacillus does not carry out the posttranslational processing characteristic of eukaryotes, Bacillus is a suitable expression host for cDNAs expressing proteins that do not require glycosylation for binding function. Suitable proteins whose binding domain loss mutants can be isolated by the subject method include, for example, the single chain anti-lysozyme antibody D1.3 described in McCafferty, J. et al. (1990) Nature 348:552–554.

Negative and positive selection steps can be carried out using the panning method or FACS, as described herein.

Equivalents

Those skilled in the art will recognize, or be able to ascertain, using no more than routine experimentation, many equivalents to the specific embodiment of the invention described herein. Such equivalents are intended to be encompassed by the following claims.

We claim:

1. A method of isolating mutant cDNAs encoding protein binding domain loss mutants, said mutant protein's wild-type analog having a first and a second binding domain with first known and second known ligands respectively thereto, and said wild-type protein having a known cDNA sequence, said method comprising the steps of:

(a) expressing vector constructs comprising said mutant cDNA in host cells to produce expression products;

(b) exposing said expression products of said host cells to a negative selection agent, said negative selection agent comprising said first ligand to said first binding domain, (c) discarding those cells containing expression product that binds to said negative selection agent;

(d) exposing said expression product of said host cells to a positive selection agent, said positive selection agent comprising said second ligand to said second binding domain;

(e) recovering said host cells of step (d);

(f) recovering said vector construct from said recovered host cells of step (e); and (g) transforming said recovered constructs of step (f) into an amplification host and amplifying said constructs.

2. The method of claim 1 wherein said mutant cDNA contains mutations encoding one amino acid mutation on average in the expression product.

3. The method of claim 1, wherein said mutant cDNA contains mutations generated by oligonucleotide directed random mutagenesis.

4. The method of claim 1, wherein said mutant cDNA contains mutations generated by oligonucleotide directed site-specific mutagenesis.

5. A method of mapping a binding domain comprising the method of claim 1 and further comprising:

(h) sequencing said cDNA of said construct of step (g);

(i) comparing the sequence obtained in step (h) with said wild type cDNA sequence to map the mutation that caused said first binding domain loss;

(j) repeating steps (a) through (i) as needed to define the first binding domain.

6. The method of claim 1, wherein said negative ligand and positive ligand are selected from the group consisting of monoclonal antibodies and substrates, wherein the negative and the positive ligand cannot both be monoclonal antibodies.

7. The method of claim 1, wherein said protein is a cell surface protein, said negative selection agent further comprises a first fluorescence label, said positive selection agent further comprises a second fluorescence label, and said steps (c) and (e) are carried out by fluorescence activated cell sorting.

8. The method of claim 1, wherein said protein is an intracellular protein, said negative selection agent further comprises a first fluorescence label, said positive selection agent further comprises a second fluorescence label, and further comprising:

treating said host cells between said steps (a) and (b) with a permeabilizing agent to render said cells permeable to first and second fluorescent labeled selection agents; and performing said steps (c) and (e) by fluorescence activated cell sorting.

9. The method of claim 1, wherein said host cell is mammalian.

10. The method of claim 1, wherein said host cell is a COS cell and said vector is piH3M.

11. The method of claim 3, wherein said oligonucleotide directed random mutagenesis is performed by the method comprising the steps:

(a) providing a wild-type cDNA template, wherein said template is located in a closed single-stranded circular DNA molecule, said single-stranded circular DNA comprising uracil;

(b) providing a randomly mutated oligonucleotide having a selected theoretical mutation frequency selected from theoretical mutation frequencies of 1–20% for each nucleotide, said oligonucleotide being hybridizable to said template under relaxed stringency;

(c) hybridizing said template to said oligonucleotide;

(d) treating the hybridization product of step (c) with polymerase and ligase to produce a heteroduplex circular DNA;

(e) amplifying said heteroduplex circular DNA under conditions where there is selection against replication of uracil-containing DNA to produce a circular duplex DNA containing a duplex mutant cDNA comprising the sequence of the mutant oligonucleotide.

12. The method of claim 11, wherein said randomly mutated oligonucleotide is produced on a DNA synthesizer by using a mixture of phosphoramidites for each nucleotide position in the oligonucleotide, wherein said mixture comprises about 95% wild-type phosphoramidite and a total concentration of contaminant phosphoramidites of about 5%.

13. The method of claim 11, wherein said single stranded circular DNA comprises an M13 origin and is produced in an Ung− host cell infected with M13 virus.

14. The method of claim 11, wherein said conditions of selection of step (e) comprise amplification in an Ung+ *E. coli*.

* * * * *

UNITED STATES PATENT AND TRADEMARK OFFICE
CERTIFICATE OF CORRECTION

PATENT NO. : 5,955,264

DATED : September 21, 1999

INVENTOR(S) : Seed and Peterson

It is certified that error appears in the above-identified patent and that said Letters Patent is hereby corrected as shown below:

At Page 2, under "Other Publications", please insert omitted reference as follows:
--Chemical Abstracts (1986) 106:360, Ref. 3687x--.
At Column 4, line 42, please delete "and" and replace with --to--.
At Column 9, line 1, please delete "Una-" and replace with --Ung---.
At Column 12, line 28, please delete "resetting." and replace with --rosetting.--.
At Column 12, line 56, please delete "resetting." and replace with --rosetting.--.

Signed and Sealed this

Third Day of April, 2001

Attest:

NICHOLAS P. GODICI

Attesting Officer    Acting Director of the United States Patent and Trademark Office